(12) United States Patent
Yasuno et al.

(10) Patent No.: US 7,756,311 B2
(45) Date of Patent: Jul. 13, 2010

(54) OPTICAL IMAGE MEASURING DEVICE, OPTICAL IMAGE MEASURING PROGRAM, FUNDUS OBSERVATION DEVICE, AND FUNDUS OBSERVATION PROGRAM

(75) Inventors: Yoshiaki Yasuno, Tsukuba (JP); Toyohiko Yatagai, Nagareyama (JP); Yasufumi Fukuma, Tokyo (JP); Hisashi Tsukada, Tokyo (JP); Tsutomu Kikawa, Tokyo (JP); Hiroyuki Aoki, Tokyo (JP); Takashi Fujimura, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 946 days.

(21) Appl. No.: 11/545,270

(22) Filed: Oct. 10, 2006

(65) Prior Publication Data

US 2010/0142780 A1 Jun. 10, 2010

(30) Foreign Application Priority Data

Oct. 12, 2005 (JP) .............................. 2005-297746
Nov. 22, 2005 (JP) .............................. 2005-337628

(51) Int. Cl.
*G06K 9/00* (2006.01)
*G01B 9/02* (2006.01)

(52) U.S. Cl. ..................................... 382/128; 356/450

(58) Field of Classification Search ................. 382/100, 382/128–131; 356/73, 326, 450, 496–498; 250/271; 359/370, 399

See application file for complete search history.

(56) References Cited

U.S. PATENT DOCUMENTS 7,227,630 B1 * 6/2007 Zavislan et al. ............. 356/244

(Continued)

FOREIGN PATENT DOCUMENTS

DE 43 09 056 A1 9/1994

(Continued)

OTHER PUBLICATIONS

Shuliang Jiao et al.: "Simultaneous acquisition of sectional and fundus opthalmic images with spectral-domain optical coherence tomography" Optics Express, Optical Society of America, Washington, DC, US, vol. 13, No. 2, Jan. 24, 2005, pp. 444-452, XP002370566; ISSN: 1094-4087, Abstract.

(Continued)

*Primary Examiner*—Samir A Ahmed
*Assistant Examiner*—Mehdi Rashidian
(74) *Attorney, Agent, or Firm*—Edwards Angell Palmer & Dodge LLP

(57) ABSTRACT

An optical image measuring device which can form a highly reliable image even if an object moves during scanning of a signal light is provided. An optical image forming device 1 comprises: an interferometer that splits a low coherence light L0 into a signal light LS and a reference light LR and generates an interference light LC by overlaying the signal light LS reflected by a fundus oculi with the reference light LR reflected by a reference mirror 14; a CCD 34 which receives the interference light LC and outputs a detection signal; Galvanometer mirrors 22 and 23 to scan the signal light LS in a main scanning direction and a sub-scanning direction; and a computer 40 forming tomographic images G1 to Gm along the main scanning direction at different positions of the sub-scanning direction. The Galvanometer mirrors 22 and 23 scan the signal light LS in a given direction crossing the main scanning direction, and the computer 40 forms a tomographic image for correction GR along the given direction to correct displacement of each topographic image Gi based on the tomographic image for correction GR.

32 Claims, 24 Drawing Sheets

U.S. PATENT DOCUMENTS

| | | | |
|---|---|---|---|
| 2004/0070822 A1* | 4/2004 | Shioda et al. | 359/372 |
| 2004/0204652 A1* | 10/2004 | Zavislan et al. | 600/476 |
| 2006/0122498 A1* | 6/2006 | Sharpe | 600/425 |
| 2007/0195308 A1* | 8/2007 | Zavislan et al. | 356/36 |

FOREIGN PATENT DOCUMENTS

| | | |
|---|---|---|
| JP | 11-325849 | 11/1999 |
| JP | 2003-000543 | 1/2003 |

OTHER PUBLICATIONS

Podoleanu A G et al: "Combined multiplanar optical coherence tomography and confocal scanning opthalmoscopy" Journal of Biomedical Optics, SPIE, Bellingham, WA, US, vol. 9, No. 1, Jan. 2004; pp. 86-93, XP002375532; ISSN: 1083-3668, Abstract.

Wojtkowski M: "In vivo human retinal imaging by Fourier domain optical coherence tomography" Journal of Biomedical Optics, SPIE, Bellingham, WA, US, vol. 7, No. 3, 2002, pp. 457-463, XP002438097; ISSN: 1083-3668, Abstract.

European Search Report; Application No. EP 06 02 1329; Nov. 6, 2007.

* cited by examiner

FIG. 25
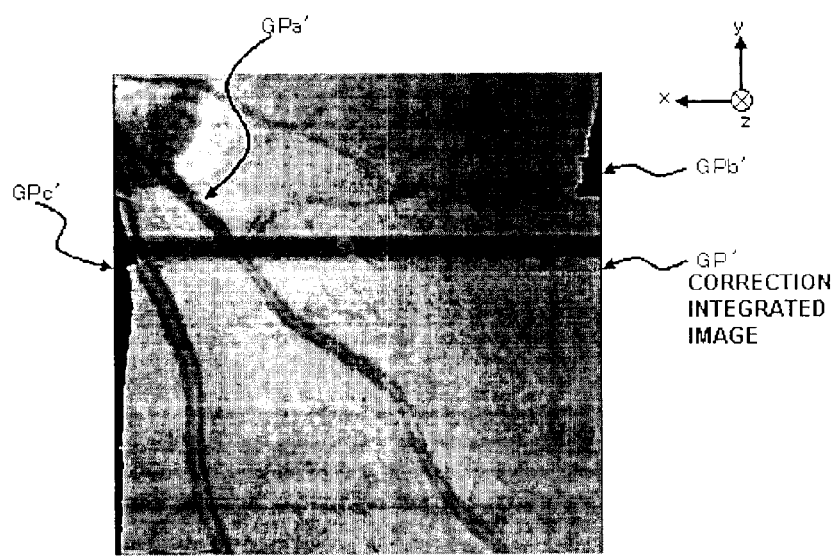
[FIG. 26]

OPTICAL IMAGE MEASURING DEVICE, OPTICAL IMAGE MEASURING PROGRAM, FUNDUS OBSERVATION DEVICE, AND FUNDUS OBSERVATION PROGRAM

BACKGROUND OF THE INVENTION

1. Field of the Invention

The present invention particularly relates to an optical image measuring device and an optical image measuring program that irradiates a light beam on an object to be measured comprising a light scattering medium and measures the surface and internal morphology of the object to be measured using the reflection light or transmitted light to form images of the object to be measured, and further relates to a fundus observation device and fundus observation program comprising this optical image measuring device for observing a fundus oculi of an eye to be examined.

2. Description of the Related Art

Optical image measuring technology which forms an image showing the surface and internal morphology of the object to be measured using a light beam from a laser source has received attention in recent years. This optical image measuring technology is expected to be developed especially in the medical field because the technology does not involve invading the human body unlike conventional X-ray CT.

JP Patent laid-open No. Hei11-325849 discloses a device in which a measuring arm scans an object with a rotary conversion mirror (Galvanometer mirror) and a reference mirror is provided on a reference arm, an interference device in which the light intensity appearing by the interference of light flux from the reference arm is also analyzed and further provided at the outlet, and a device which gradually changes the light flux phase of a reference light with discontinuous values and which is provided on the reference arm.

This device uses the method of so-called "Fourier Domain OCT (Optical Coherence Tomography)" in which DE Patent laid-open No. DE4309056A is a basic technology. That is, a form in the depth direction (z-direction) of an object to be measured is imaged by irradiating a light beam on an object to be measured, obtaining the spectrum intensity distribution of the reflection light, and Fourier transforming it.

Further, the device described in JP Patent laid-open No. Hei11-325849 comprises a Galvanometer mirror which scans a light beam (signal light) and thereby the image in the desired measured region of the object to be measured. However, since this device scans a light beam in only one direction perpendicular to the z-direction, the formed image will be a 2-dimensional tomographic image in the depth direction (z-direction) along the scanning direction (x-direction) of the light beam.

In addition, JP Patent laid-open No. 2003-543 discloses an application example of such a device in the ophthalmic field.

When an optical image measuring device configured to scan with such a light beam is applied to living bodies such as the eyes, it is necessary to consider movement of the living body during light beam scanning. In other words, if the living body moves during scanning, displacement in each measuring position with the light beam (each measuring position in the x-direction in JP Patent laid-open No. Hei11-325849) occurs, resulting in distortion of the image.

For example, scanning of the light beam for conducting an image measurement of a living eye (fundus oculi) takes around 2.5 to 3.5 seconds. If the position of a living eye is displaced by, for example, a heartbeat or eye movement during scanning, the formed image will be distorted in the displacement direction of the living eye or a part of the image will be interrupted, and thus, the accuracy of the image will be impaired.

Therefore, means to correct this distortion of the image are necessary to enhance the accuracy of image measuring of the living body. However, conventional optical image measuring devices as described above could not correct the distortion of the image due to movement of the living body.

The present invention solves such problems, and is intended to provide an optical image measuring device, an optical image measuring program, a fundus observing device, and a fundus observing program which can form a highly accurate image even if the object to be measured moves during scanning of the light beam.

SUMMARY OF THE INVENTION

To achieve said purpose, the first aspect of the present invention is an optical image measuring device comprising: a light source; an interference light generating means for splitting the light output from said light source into a signal light directed toward an object to be measured and an reference light directed toward a reference object, and also for generating an interference light by overlaying the signal light that has passed through said object to be measured and the reference light that has passed through said reference object; a detecting means for outputting a detection signal upon receipt of said generated interference light; a scanning means for scanning the incident position of said signal light with respect to said object to be measured in a given main scanning direction and in a sub-scanning direction perpendicular to the main scanning direction respectively; and an image processing means for forming an image in the depth direction of said object to be measured at said incident position on the basis of said detection signal based on the interference light formed by said signal light that has passed through the incident position and said reference light and for forming a tomographic image along said two or more main scanning directions at different positions in said sub-scanning direction by forming the tomographic image along said main scanning direction based on said image at each of said formed incident positions, for each of a plurality of said incident positions along said main scanning direction; wherein said scanning means scans said signal light in the given direction crossing with said main scanning direction, and said image processing means forms a tomographic image for correction along said given direction and corrects the displacement of each of said two or more formed tomographic images based on said tomographic image for correction.

The second aspect of the present invention is an optical image measuring program for controlling an optical image measuring device comprising: a light source; an interference light generating means for splitting the light output from said light source into a signal light directed toward an object to be measured and an reference light directed toward a reference object, and also for generating an interference light by overlaying the signal light that has passed through said object to be measured and the reference light that has passed through said reference object; a detecting means for outputting a detection signal upon receipt of said generated interference light; a scanning means for scanning the incident position of said signal light with respect to said object to be measured in a given main scanning direction and in a sub-scanning direction perpendicular to the main scanning direction respectively; and an image processing means for forming an image in the depth direction of said object to be measured at said incident position on the basis of said detection signal based on the interference light generated by said signal light that has passed through the incident position and said reference light and for forming a tomographic image along said two or more main scanning directions at different positions in said sub-scanning direction by forming the tomographic image along said main scanning direction based on said image at each of said formed incident positions, for each of a plurality of said incident positions along said main scanning direction; wherein said scanning means is controlled so as to scan said signal light in the given direction crossing with said main scanning direction, and said image processing means is made to form a tomographic image for correction along said given direction and to correct the displacement of each of said two or more formed tomographic images based on said tomographic image for correction.

The third aspect of the present invention is a fundus observation device comprising: a first image forming means for forming a 2-dimensional image of the surface of a fundus oculi of an eye to be examined; and a second image forming means for forming a tomographic image of said fundus oculi; wherein said fundus observation device comprises the first image processing means for generating an integrated image by integrating tomographic images formed by said second image forming means in the depth direction, for detecting displacement in the direction perpendicular to said depth direction of said generated integrated image based on said 2-dimensional image formed by said first image forming means, and for correcting the displacement of said tomographic images in said perpendicular direction based on said detected displacement.

The fourth aspect of the present invention is a fundus observing device comprising: a first image forming means for forming a 2-dimensional image of the surface of a fundus oculi of an eye to be examined; a light source; an interference light generating means for splitting the light output from said light source into a signal light directed toward said fundus oculi and interference light directed toward a reference object, and also for generating interference light by overlaying the signal light that has passed through said fundus oculi and the reference light that has passed through said reference object; a detecting means for outputting a detection signal upon receipt of said generated interference light; a scanning means for scanning the incident position of said signal light with respect to said fundus oculi in a given main scanning direction and in a sub-scanning direction perpendicular to the main scanning direction respectively; and the second image forming means for forming an image in the depth direction of said fundus oculi at the incident position on the basis of said detection signal based on the interference light formed by said signal light that has passed through the incident position and said reference light and for forming a tomographic image along said two or more main scanning directions at different positions in said sub-scanning direction by forming the tomographic image along said main scanning direction based on said image at each formed incident position, for each of a plurality of said incident positions along said main scanning direction; wherein, said fundus observing device comprises: a first image processing means for generating each integrated image of said two or more tomographic images by integrating each said two or more tomographic images formed by said second image forming means in said depth direction, for detecting displacement in the direction perpendicular to said depth direction of said formed two or more integrated images based on said 2-dimensional image formed by said first image forming means, and for correcting each displacement of said two or more tomographic images in said perpendicular direction based on said detected displacement; a control means for controlling said scanning means of said second image forming means so as to scan said signal light in the given direction crossing with said main scanning direction; and a second image processing means for forming a tomographic image for correction along said given direction and also for correcting the displacement in said depth direction of each of said formed two or more tomographic images based on said tomographic image for correction.

The fifth aspect of the present invention is a fundus observing program that creates a fundus observing device comprising a first image forming means for forming a 2-dimensional image of the surface of a fundus oculi of an eye to be examined and a second image forming means for forming a tomographic image of said fundus oculi and which functions so as to generate an integrated image by integrating tomographic images formed by said second image forming means in the depth direction, detect displacement in the direction perpendicular to said depth direction of said generated integrated image based on said 2-dimensional image formed by said first image forming means, and correct the displacement of said tomographic images in said perpendicular direction based on said detected displacement.

The sixth aspect of the present invention is a fundus observing program that creates a fundus observing device comprising a first image forming means for forming a 2-dimensional image of the surface of a fundus oculi of an eye to be examined; a light source; an interference light generating means for splitting the light output from said light source into a signal light directed toward said fundus oculi and an interference light directed toward a reference object, and also for generating an interference light by overlaying the signal light that has passed through said fundus oculi and the reference light that has passed through said reference object; a detecting means for outputting a detection signal upon receipt of said generated interference light; a scanning means for scanning the incident position of said signal light with respect to said fundus oculi in a given main scanning direction and in a sub-scanning direction perpendicular to the main scanning direction respectively; and a second image forming means for forming an image in the depth direction of said fundus oculi at the incident position on the basis of said detection signal based on the interference light formed by said signal light that has passed through the incident position and said reference light and for forming a tomographic image along said two or more main scanning directions at different positions in said sub-scanning direction by forming the tomographic image along said main scanning direction based on said image at each formed incident position, for each of a plurality of said incident positions along said main scanning direction; to function as the first image processing means for generating each integrated image of said two or more tomographic images by integrating each of said two or more tomographic images formed by said second image forming means in said depth direction, for detecting displacement in the direction perpendicular to said depth direction of said formed two or more integrated images based on said 2-dimensional image formed by said first image forming means, and for correcting each displacement of said two or more tomographic images at said perpendicular direction based on said detected displacement; a control means for controlling said scanning means of said second image forming means so as to scan said signal light in the given direction crossing with said main scanning direction; and the second image processing means for forming a tomographic image for correction along said given direction and for correcting the displacement at said depth direction of each of said formed two or more tomographic images based on said tomographic image for correction.

EFFECTS OF THE INVENTION

According to the optical image measuring device and the optical image measuring program related to the present invention, since a scanning means is configured to scan said signal light in the given direction crossing with said main scanning direction and an image processing means is configured to form a tomographic image for correction along said given direction and correct displacement of each of said two or more formed tomographic images based on said tomographic image for correction, displacement of each tomographic image can be corrected even if the object to be measured moves during scanning of the signal light (light beam), and thus, a highly accurate image can be formed.

According to the fundus observation device and the fundus observation program related to the present invention, an integrated image is generated by integrating a tomographic image formed by the second image forming means in the depth direction, and displacement in the direction perpendicular to the depth direction of this integrated image based on the 2-dimensional image formed by the first image forming means. Further, they function so as to correct displacement of the tomographic image in the direction perpendicular to the depth direction based on the detected displacement. As a result, since displacement in the direction perpendicular to the depth direction of the tomographic image can be corrected even if the object to be measured moves during scanning of the signal light, a highly accurate image can be formed.

Also, according to the fundus observation device and the fundus observation program related to the present invention, each integrated image is generated by integrating each tomographic image formed by the second image forming means in the depth direction, and displacement in the direction perpendicular to the depth direction of each integrated image based on the 2-dimensional image formed by the first image forming means. Moreover, they correct displacement of each tomographic image in the direction perpendicular to the depth direction based on the detected displacement. Further, they function so as to scan the signal light in the given direction crossing with the main scanning direction by controlling the scanning means of the second image forming means, form the tomographic image for correction along the given direction, and correct displacement in the depth direction of each tomographic image based on this tomographic image for correction. As a result, since both displacements in the direction perpendicular to the depth direction of the tomographic image and displacement in the depth direction can be corrected even if the object to be measured moves during scanning of the signal light, a highly accurate image can be formed.

BRIEF DESCRIPTION OF THE DRAWINGS

In the accompanying drawings:

FIG. 4 (A) represents one example of the scanning features of a signal light when a fundus oculi is seen from the incident side (−z-direction) of a signal light. FIG. 4 (B) represents one example of the arrangement features of a scanning point on each scanning line.

FIG. 25 is a diagram representing one correction integrated image generated by a preferred embodiment of the fundus observation device related to the present invention.

FIG. 26 is a diagram representing one fundus oculi surface image before correcting the displacement by a preferred embodiment of the fundus observation device related to the present invention.

DETAILED DESCRIPTION OF THE REFERENCE EMBODIMENTS

One example of preferred embodiments of an optical image measuring device, an optical image measuring program, a fundus observation device, and a fundus observation program, related to the present invention is described in detail referring to figures.

Device Constitution

Figure 1:
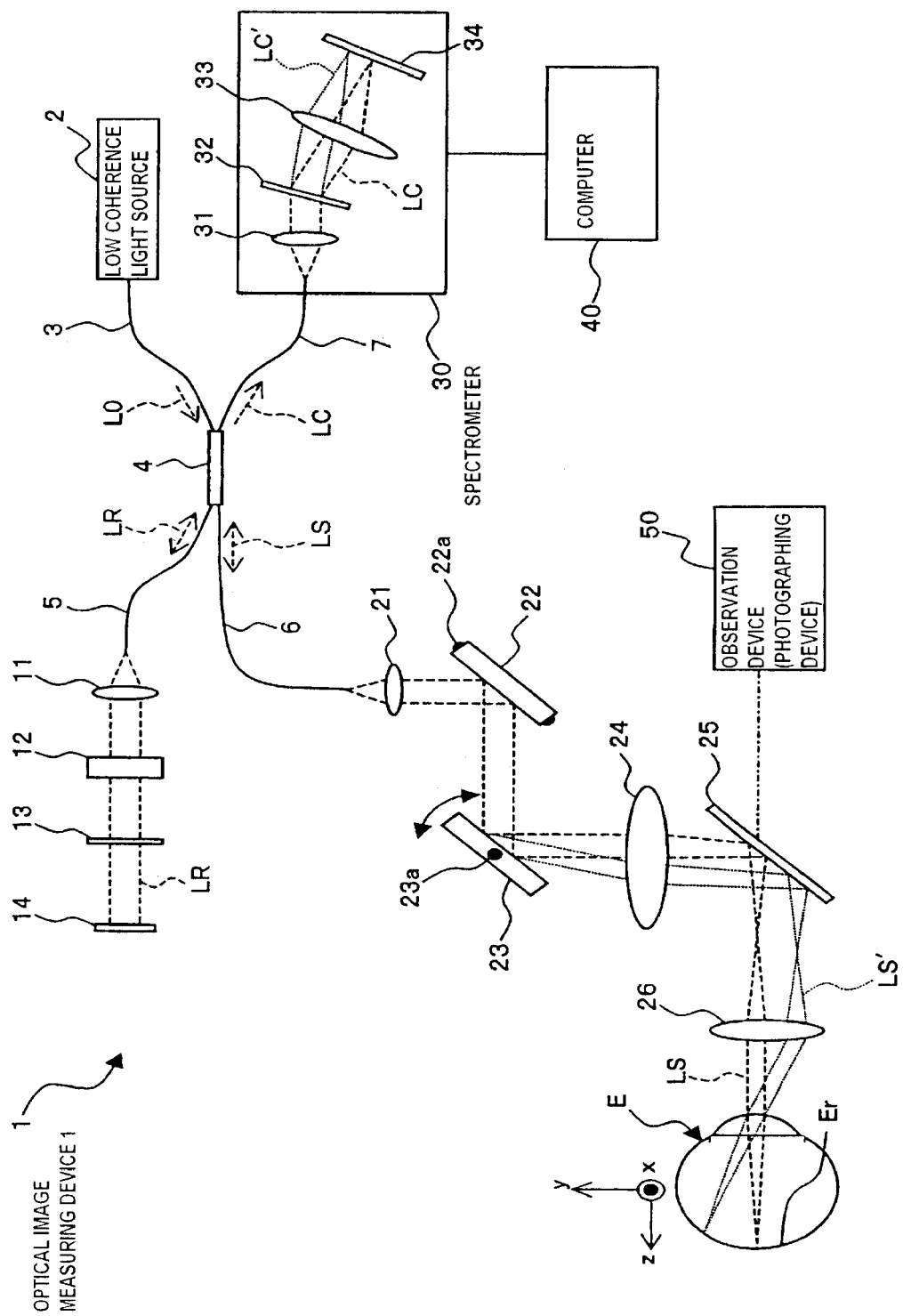
FIG. 1 is a schematic diagram representing one example of the entire constitution of a preferred embodiment of the optical image measuring device related to the present invention.

FIG. 1 represents one example of the entire constitution of the optical image measuring device related to the present invention. An optical image measuring device 1 shown in the same figure is configured substantially the same as conventional ones, comprising an interferometer that splits the laser light output from a laser light source into reference light and signal light, and generating interference light by overlaying the reference light that has passed through a reference object and the signal light that has passed through an object measured to be measured, and is configured to form images of the object to be measured by analyzing the detection results of this interference light.

A low coherence light source 2 comprises broad band light sources such as a super luminescent diode (SLD) or a light emitting diode (LED) outputting a low coherence light L0. This low coherence light L0 is a light, for example, having a wave length in the near-infrared region and a temporal coherence length of approximately several tens of micrometers.

The low coherence light L0 output from the low coherence light source 2 is guided to an optical coupler 4 through an optical fiber 3 composed of, e.g. a single mode fiber, and then split into reference light LR and signal light LS.

Furthermore, the optical coupler 4 has both actions, i.e. a means for splitting the light (splitter), and a means for overlaying the light (coupler); however, herein it is conventionally referred to as an "optical coupler."

The reference light LR is guided by an optical fiber 5 and emitted from the fiber end. The reflected reference light LR is reflected by a reference mirror 14 (reference object) through a glass block 12 and a density filter 13 after having been converged into a parallel light flux by a collimator lens 11.

The reference light LR reflected by the reference mirror 14 is converged to the fiber end of the optical fiber 5 by the collimator lens 11 again through the density filter 13 and the glass block 12. The converged reference light LR is guided to the optical coupler 4 through the optical fiber 5.

Furthermore, the glass block 12 and the density filter 13 act as a delaying means to match the optical path length (optical distance) between the reference light LR and the signal light LS, and as a means to match the dispersion characteristics of the reference light LR and the signal light LS.

On the other hand, the signal light LS is emitted from the fiber end by being guided with an optical fiber 6, and is converted into a parallel light flux with a collimating lens 21. The signal light LS which is converted into a parallel light flux is reflected by a Galvanometer mirror 22 and further reflected by a Galvanometer mirror 23.

The Galvanometer mirrors 22 and 23 are rotated around rotary shafts 22a and 23a respectively. The rotary shafts 22a and 23a are arranged so as to be perpendicular to each other. The rotary shaft 22a of the Galvanometer mirror 22 is arranged so as to be parallel to the page of FIG. 1 and to be a given angle (e.g., 45 degrees) to the traveling direction of the signal light LS. On the other hand, the rotary shaft 23a of the Galvanometer mirror 23 is arranged to be perpendicular to the page of FIG. 1. That is, the Galvanometer mirror 23 is rotatable in the direction shown in FIG. 1 with the double-headed arrow, while the Galvanometer mirror 22 is rotatable perpendicular to the double-headed arrow. As a result, the Galvanometer mirrors 22 and 23 are functioned so as to change the reflection direction of the signal light LS to the direction perpendicular to each other. The concrete reflection mode of the signal light LS with these Galvanometer mirrors 22 and 23 will be described later.

The signal light LS reflected by the Galvanometer mirror 23 is condensed with a lens 24 while being reflected by a dichroic mirror 25 to form an image and enters an eye to be examined E through an objective lens 26. The signal light entering the eye to be examined E forms an image on a fundus oculi (retina) Er and is reflected.

The signal light LS at this time is not only reflected on the surface of the fundus oculi Er, but also reaches the deep region of the fundus oculi Er and is scattered at the reflective index boundary. As a result, the fundus oculi reflection light of the signal light LS becomes light including information indicating the surface mode of fundus oculi Er and information indicating the state of backward scattering in the reflective index boundary of a deep tissue.

Wherein, the dichroic mirror 25 functions so as to reflect light in the (near) infrared region and transmit light within the visible area.

The signal light LS reflected by the fundus oculi Er passes the objective lens 26, the dichroic mirror 25, the lens 24, the Galvanometer mirrors 22 and 23, and is condensed at the fiber end of the optical fiber 6 with the collimating lens 21. The condensed signal light LS is led to the optical coupler 4 through the optical fiber 6.

The optical coupler 4 overlays the reference light LR returned by reflecting on the reference mirror 14 with the signal light LS returned by reflecting on the fundus oculi Er in the eye to be examined E to generate the interference light LC. The generated interference light LC is guided into a spectrometer 30 through an optical fiber 7.

Herein, the "interference light generating means" in the present invention is comprised of an interferometer including at least the optical coupler 4, the optical fibers 5 and 6, and the reference mirror 14.

The spectrometer 30 is comprised of a collimating lens 31, a diffraction grating 32, an image forming lens 33, and a CCD (Charge Coupled Device) 34. The diffraction grating 32 is a transmission type diffraction grating; however, needless to say, a reflection type diffraction grating may also be used. Furthermore, needless to say, in place of CCD 34, it is also possible to use other photo-detecting elements (detecting means).

The interference light LC made incident onto the spectrometer 30 is to be split (spectral resolution) by the diffraction grating 32 after having been converged into a parallel light flux by the collimator lens 31. The split interference light LC forms an image on the image pick-up surface of the CCD 34 by the image forming lens 33. The CCD 34 receives this interference light LC that is to be converted to an electrical detection signal, and outputs this detection signal to a computer 40.

This computer 40 analyzes the detection signal input from the CCD 34 and performs a process of forming tomographic images of a fundus oculi Er of the eye to be examined E. The analysis technique then is the same technique as the conventional Fourier domain OCT technique. The tomographic image formation processing with the computer 40 which is particular to the present invention will be described later.

Furthermore, the computer 40 executes control of each part of the optical image measuring device 1. For example, it controls the rotary movement of the Galvanometer mirrors 22 and 23, the operation of the alignment mechanism of the optical image measuring device 1 (not shown) for the eye to be examined E, and the output of the low coherence light with the low coherence light source 2.

An observation device (photographing device) 50 is, for example, any observation device and/or photographing device such as a slit lamp (slit-lamp microscope) and a fundus camera used in the ophthalmic field. This observation device 50 may be arranged integrally with or separately from the optical image measuring device 1. An examiner can manually align the optical image measuring device 1 for the eye to be examined E, confirm the state of the fundus oculi Er in the measurement, and photograph the fundus oculi Er while observing the eye to be examined E with the observation device 50.

Regarding the Signal Light Scanning

As described above, the reflection direction of the signal light LS is changed with the Galvanometer mirrors 22 and 23. By changing the direction of the reflecting surfaces of the Galvanometer mirrors 22 and 23 respectively, the signal light 23 can be irradiated on various positions of the fundus oculi Er. That is, the signal light LS can be scanned in the fundus oculi Er. The Galvanometer mirrors 22 and 23 correspond to an example of "scanning means" of the present invention.

The signal light LS shown by broken lines and a signal light LS' shown by dotted lines in FIG. 1 represent signal lights advancing two different optical paths corresponding to the change in the direction of the Galvanometer mirror 23.

The signal light LS' shown by dotted lines represents the signal light when the direction of the Galvanometer mirror 23 in the above described [Device Constitution] is changed at a certain angle to the bottom direction of the page in FIG. 1 (−y direction). The signal light LS' after changing the direction is condensed at the position departing upward (+y direction) from the center position of the fundus oculi Er compared with when the signal light LS before changing the direction is condensed at the near center position of the fundus oculi Er. In this case, the signal light LS which is reflected at the fundus oculi Er is a light including information (information on the surface and the deep part) at the near center position of the fundus oculi Er, while the reflection light of the signal light LS' is a light including information (information on the surface and the deep part) at the position departing in the +y direction from the fundus center.

Therefore, by rotating the Galvanometer mirror 23 in the +y direction in FIG. 1 (that is, changing the direction of the reflecting surface so as to make the incident angle of the signal light small), the condensing position of the signal light on the fundus oculi Er can be shifted in the −y direction. Conversely, by rotating the Galvanometer mirror 23 in the −y direction (that is, changing the direction of the reflecting surface so as to make the incident angle of the signal light large), the condensing position of the signal light on the fundus oculi Er can be shifted in the +y direction.

Likewise, by rotating the Galvanometer mirror 22 to the front side of the page (+x direction) in FIG. 1, the condensing position of the signal light on the fundus oculi Er can be shifted to the back side of the page (−x direction), while by rotating the Galvanometer mirror 22 in the −x direction, the condensing position of the signal light on the fundus oculi Er can be shifted in the +x direction.

In addition, by rotating both Galvanometer mirrors 22 and 23 simultaneously, the condensing position of the signal light can be shifted in the direction in which the x-direction and y-direction are composed. That is, by controlling two Galvanometer mirrors 22 and 23 respectively, the signal light can scan in any direction on the x, y plane.

Constitution of the Control System

Figure 2:
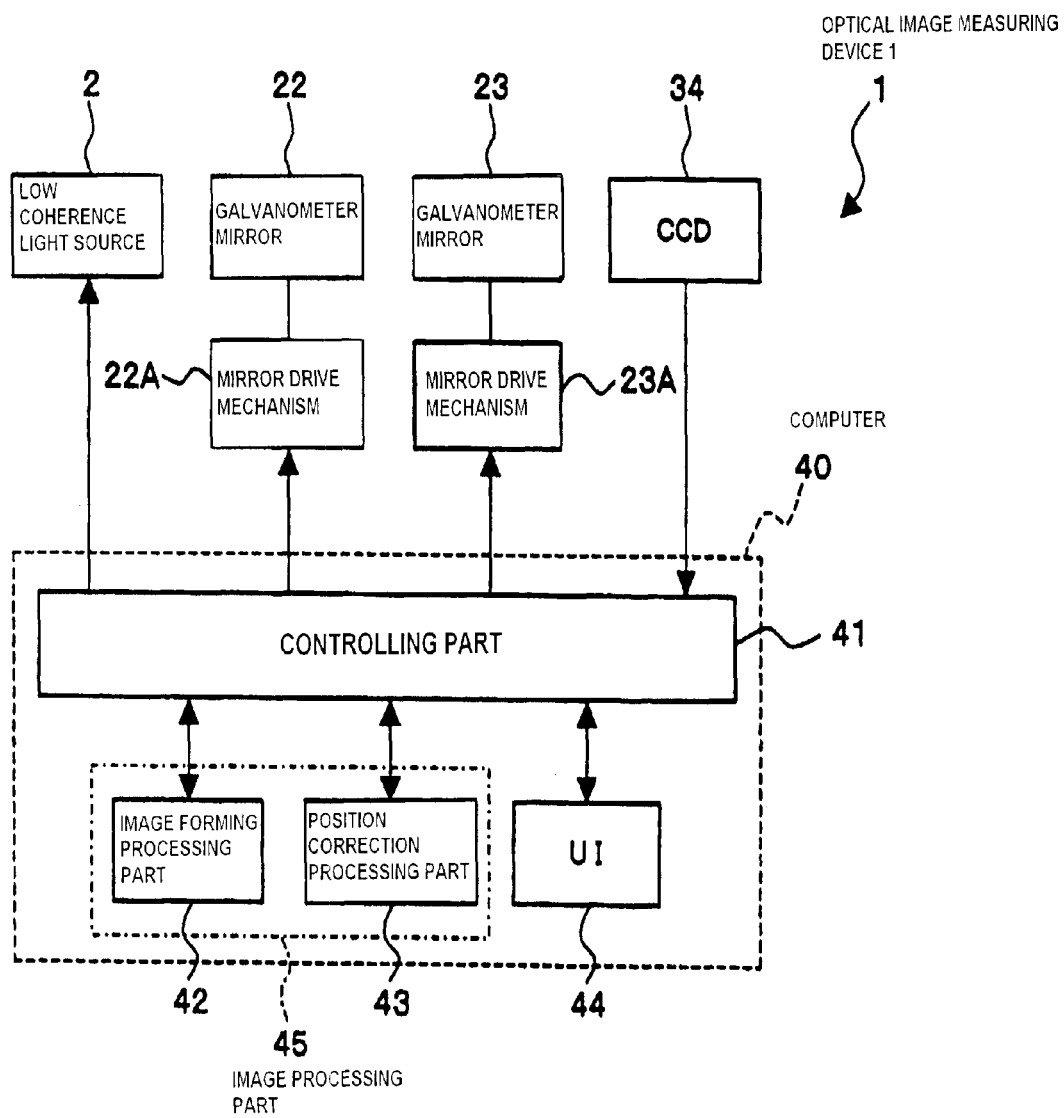
FIG. 2 is a schematic block diagram representing one compositional example of a preferred embodiment of the optical image measuring device related to the present invention.
Figure 3:
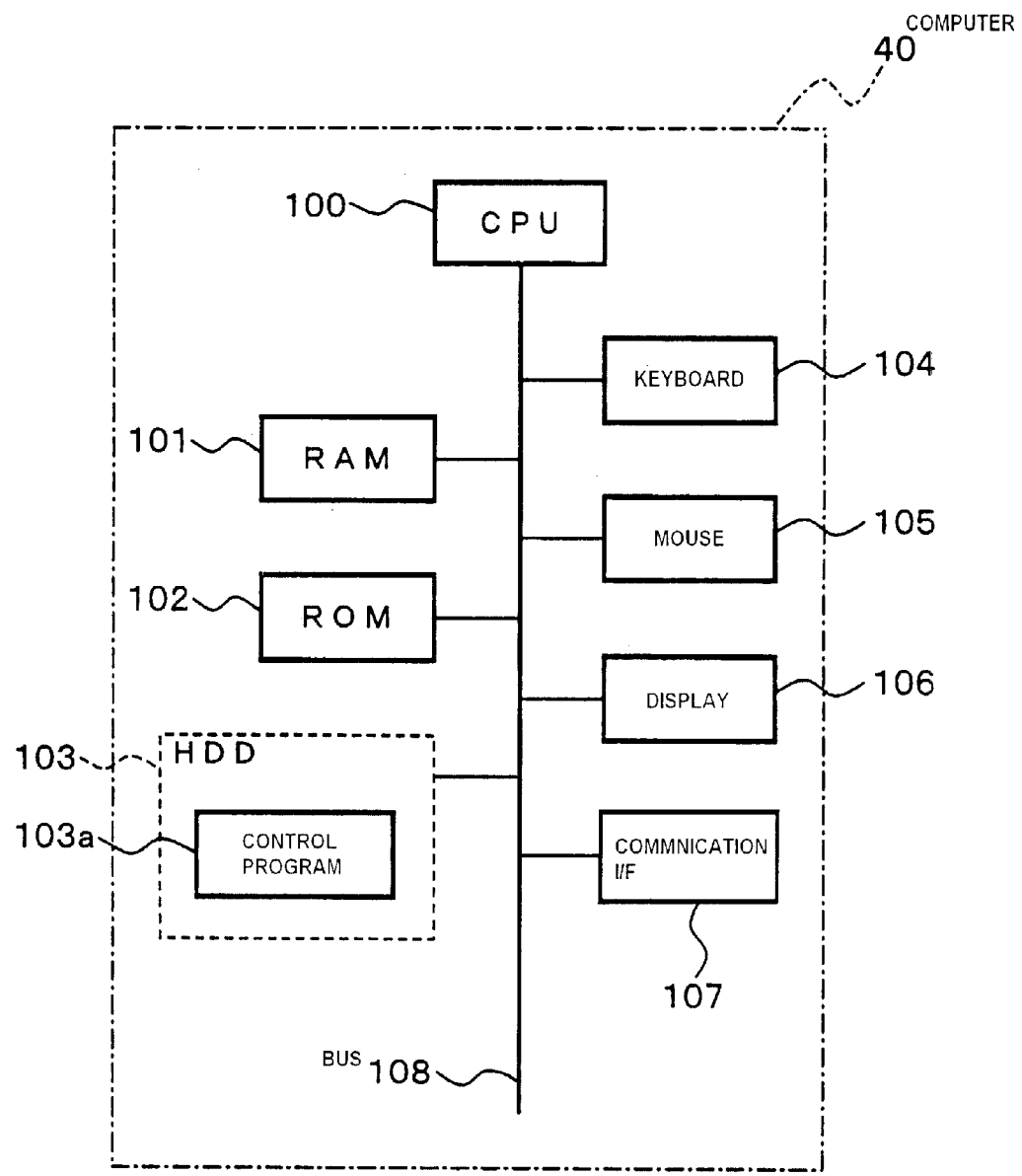
FIG. 3 is a schematic block diagram representing one example of the hardware configuration of a computer in a preferred embodiment of the optical image measuring device related to the present invention.

The constitution of the control system in the optical image measuring device 1 of the present embodiment is described. FIG. 2 and FIG. 3 show an example of the constitution of the control system in the optical image measuring device 1 respectively. FIG. 2 represents the functional constitution of the control system in the optical image measuring device 1. FIG. 3 represents the hardware configuration of the computer 40.

Hardware Configuration of the Computer

First, the hardware configuration of the computer 40 is described referring to FIG. 3. The computer 40 comprises the hardware configuration which is the same as a conventional computer. Specifically, it is comprised including a CPU 100 (microprocessors), a RAM 101, a ROM 102, a hard disk drive (HDD) 103, a keyboard 104, a mouse 105, a display 106, and a communication interface (I/F) 107. These parts are connected through a bus 108.

The CPU 100 executes characteristic operations in the present invention by deploying a control program 103a stored in the hard disk drive 103 on the RAM 101. Wherein, this control program 103a corresponds to an example of an "optical image measuring program" of the present invention.

The CPU 100 executes control of each part of the device and various arithmetic processing. For example, it executes control of the above-mentioned low coherence light source 2 and the Galvanometer mirrors 22 and 23 as well as control of each part of the device corresponding to an operation signal from the keyboard and the mouse 105, the display processing with the display 106, and the sending and receiving processing of data and control signals with the communication interface 107.

The keyboard 104, the mouse 105, and the display 106 are used as a user interface of the optical image measuring device 1. The keyboard 104 is used as a device for typing to enter characters and numbers. The mouse 105 is used as a device to input various operations to the display screen of the display 106.

The display 106 is any display device such as LCD (Liquid Crystal Display) or CRT (Cathode Ray Tube), and displays an image of the eye to be examined E formed by the optical image measuring device 1 and various operation screens and setting screens. The display 106 may be arranged so as to be mounted on the outside of the chassis of the optical image measuring device 1, or arranged as a monitor device as with conventional computers.

However, the user interface in the optical image measuring device 1 is not limited to such a constitution, but may be configured with any user interface means such as a track ball, a joy-stick, a touch panel LCD, and a control panel for ophthalmic examination which includes functions to display various information and input various information.

The communication interface 107 performs processing to send a control signal from the CPU 100 to each part of the device such as the low coherence light source 2 and the Galvanometer mirror 22, and to receive a detection signal from CCD 34. Moreover, when the computer 40 is connected to a network such as LAN (Local Area Network) or Internet, etc., the communication interface 107 may be configured to be equipped with a network adopter such as LAN card, etc. or communication equipment such as modem, etc. so as to be able to perform data communication through the network.

Functional Constitution

Next, referring to FIG. 2, the constitution of a control system of the optical image measuring device 1 is described.

The optical image measuring device 1 is provided with a mirror drive mechanism 22A to rotatably drive the Galvanometer mirror 22 and a mirror drive mechanism 23A to rotatably drive the Galvanometer mirror 23. The mirror drive mechanisms 22A and 23A comprise respectively a constitution the same as conventional ones, a driving device such as a stepping motor, and a power transmission mechanism to transmit the power generated with this driving device to the Galvanometer mirrors 22 and 23.

The computer 40 comprises a controlling part 41, an image forming part 42, a position correction processing part 43, and a user interface (UI) 44, based on the hardware configuration shown in FIG. 3. The image forming part 42 and the position correction processing part 43 form an image processing part 45 to perform various image processing. This image processing part 45 corresponds to an example of the "image processing means" of the present invention.

The controlling part 41, the image forming part 42, and the position correction processing part 43 are comprised respectively including the CPU 100 that executes a control program 103a. The controlling part 41 is also comprised including a storing device such as the RAM 101, the ROM 102, and the HDD 103. The user interface 44 is comprised including the keyboard 104, the mouse 105, and the display 106.

The controlling part 41 sends a control signal to the coherence light source 2 and the mirror drive mechanisms 22A and 23A respectively. The low coherence light source 2 switches the output start and stop of the low coherence light L0 and adjusts the output intensity based on a control signal from the controlling part 41. The mirror drive mechanism 22A (the mirror drive mechanism 23A) drives the Galvanometer mirror 22 (the Galvanometer mirror 23) to rotate it at an angle required by the control signal based on a control signal from the controlling part 41.

In addition, the controlling part 41 receives a detection signal from the CCD 34 and performs processing to provide it to the image forming part 42 and the position correction processing part 43. Further, the controlling part 41 controls the operation of each part of the device based on an operation signal from the user interface 44 and display processing of an image and a screen with the user interface 44.

The image forming part 42 performs processing to form an image (tomographic image) of the fundus oculi Er in the eye to be examined E based on a detection signal of the CCD 34 provided from the controlling part 41. An example of a concrete mode of processing to obtain a detection signal in the CCD 34 and of the image forming part 42 are described specifically.

Regarding Obtaining Processing of a Detection Signal

A detection signal from the CCD 34 is generated in response to scanning of the signal light LS. The controlling part 41 controls the Galvanometer mirrors 22 and 23 to shift a scanning point of the signal light LS on the fundus oculi Er (an incident target position (condensing target position) of the signal light LS on the fundus oculi Er)) in order. While it controls the low coherence light source 2 to continuously switch the output start and stop of the low coherence light L0 at a given timing (synchronized with the shift of a scanning point). As a result, the signal light LS is condensed on a plurality of scanning points on the fundus oculi Er and scanned so as to enter the deep tissue thereof.

Figure 4A:
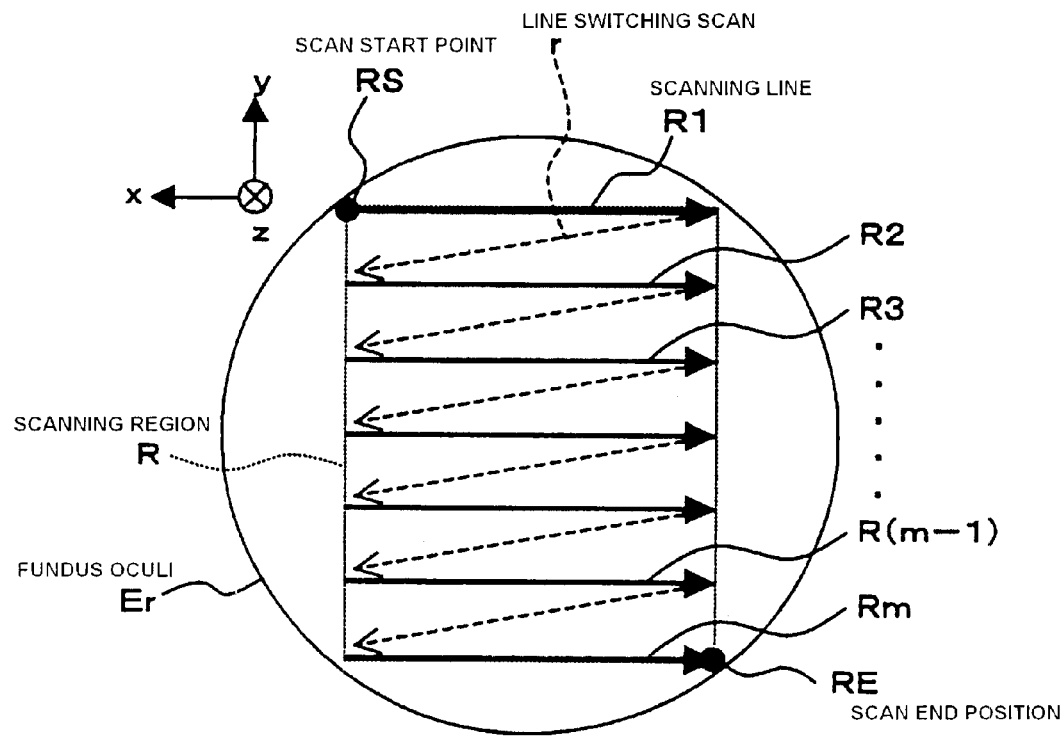
FIG. 4 is a schematic diagram representing one example of the scanning features of a signal light by a preferred embodiment of the optical image measuring device related to the present invention.
Figure 4B:
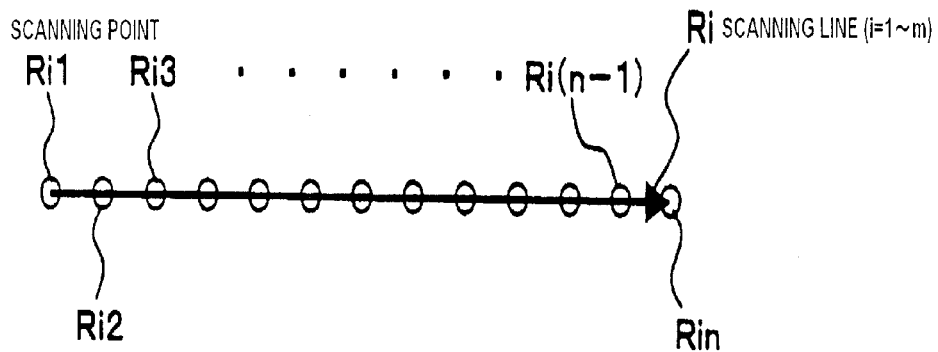

FIG. 4 represents an example of the scanning features of the signal light LS. FIG. 4 (A) represents one example of the scanning features of the signal light LS when the fundus oculi Er is seen from the incident side (−z direction) of the signal light LS. FIG. 4 (B) represents one example of the arrangement features of a scanning point on each scanning line.

As shown in FIG. 4 (A), the signal light LS is scanned within a rectangular shaped scanning region R that has been preset. Within this scanning region R, a plurality of (m number of) scanning lines R1 through Rm have been set in the −x direction. When the signal light LS is scanned along each scanning line Ri (i=1 through m), detection signals of interference light LC are generated (described later).

Herein, the direction of each scanning line Ri is referred to as the "main scanning direction" and the orthogonally crossing direction is referred as the "sub-scanning direction". Therefore, the scanning of the signal light LS in a main scanning direction is performed by the Galvanometer mirror 22, and the scanning in the sub-scanning direction is performed by the Galvanometer mirror 23.

On each scanning line Ri, as shown in FIG. 4 (B), a plurality of (n number of) scanning points Ri1 through Rin have been preset.

First, the controlling part 41 controls the Galvanometer mirrors 22 and 23 to set the incident target of the signal light LS at a scan start point RS (scanning point R11) on the first scanning line R1. The low coherence light source 2 is controlled to flash the low coherence light L0 for emitting the signal light LS to the scan start point RS. The CCD 34 receives the interference light LC based on the reflection light and outputs detection signals to the controlling part 41.

Next, by controlling the Galvanometer mirror 22, the controlling part 41 sets the incident target of the signal light LS at the scanning point R12, and triggering a flash emission of the low coherence light L0 for making the signal light LS incident onto the scanning point R12. The CCD 34 receives the interference light LC based on the reflection light, and then outputs the detection signal.

Likewise, detection signals output from the CCD 34 are obtained by flash emitting the low coherence light L0 at each scanning point while shifting the incident target of the signal light LS from scanning point R13, R14, ..., R1 (n−1), R1n in order.

Once the measurement at the last scanning point R1n of the first scanning line R1 is finished, the controlling part 41 controls the Galvanometer mirrors 22 and 23 simultaneously and shifts the incident target of the signal light LS to the first scanning point R21 of the second scanning line R2 following a line switching scan r. Then, by conducting a measurement at each scanning point R2j (j=1 through n) of this second scanning line R2 as well, a detection signal corresponding to each scanning point R2j is obtained.

Likewise, measurements are conducted with respect to the third scanning line R3, . . . , the m–1th scanning line R (m–1), the mth scanning line Rm respectively to obtain the detection signals corresponding to each scanning point. As a result, the controlling part 41 obtains m×n number of detection signals corresponding to m×n number of scanning points Rij (i=1 through m, j=1 through n) within the scanning region R. Hereinafter, a detection signal corresponding to the scanning point Rij may be represented as Dij.

Such interlocking control of such shifting of scanning points and the output of the low coherence light L0 is performed by synchronizing, for instance, the transmitting timing of control signals with respect to the mirror drive mechanisms 22A, 23A and the transmitting timing of control signals (output request signal) with respect to the low coherence light source 2.

Regarding Image Formation Processing

The image forming part 42, similar to conventional ones, forms a tomographic image of the fundus oculi Er along each scanning line Ri by performing two steps of arithmetic processing. In the first step of the arithmetic process, based on the detection signal Dij corresponding to each scanning point Rij, the image forming part 42 forms an image in the depth direction (z-direction shown in FIG. 1) of the fundus oculi Er at the scanning point Rij. In the second step of the arithmetic process, with regard to each scanning line Ri, based on the images in the depth direction at n number of scanning points Ri1 through Rin thereon, a tomographic image Gi of a fundus oculi Er along this scanning line Ri is formed.

That is, the first phase is an arithmetic process to form an image in the depth direction (z-direction) of the fundus oculi Er in the incident position based on the detection signal Dij on the basis of the interference light generated from the signal light LS and the reference light LR passing the incident position for each of the n number of incident positions (scanning point Rij) of the signal light LS along the main scanning direction (direction of the scanning line Ri). Whereas, the second phase is an arithmetic process to form a tomographic image along the main scanning direction based on an image at each incident position formed in the first phase. As a result, m number of tomographic images at different positions in the sub-scanning direction (y-direction) are obtained.

In addition, the image forming part 42 performs formation processing of a 3-dimensional image showing the surface and internal morphology of the fundus oculi Er based on m number of tomographic images obtained with said arithmetic processing. This 3-dimensional image formation processing can be performed by, for example, a method similar to conventional ones such that it performs interpolation processing between adjacent tomographic images.

Figure 5:
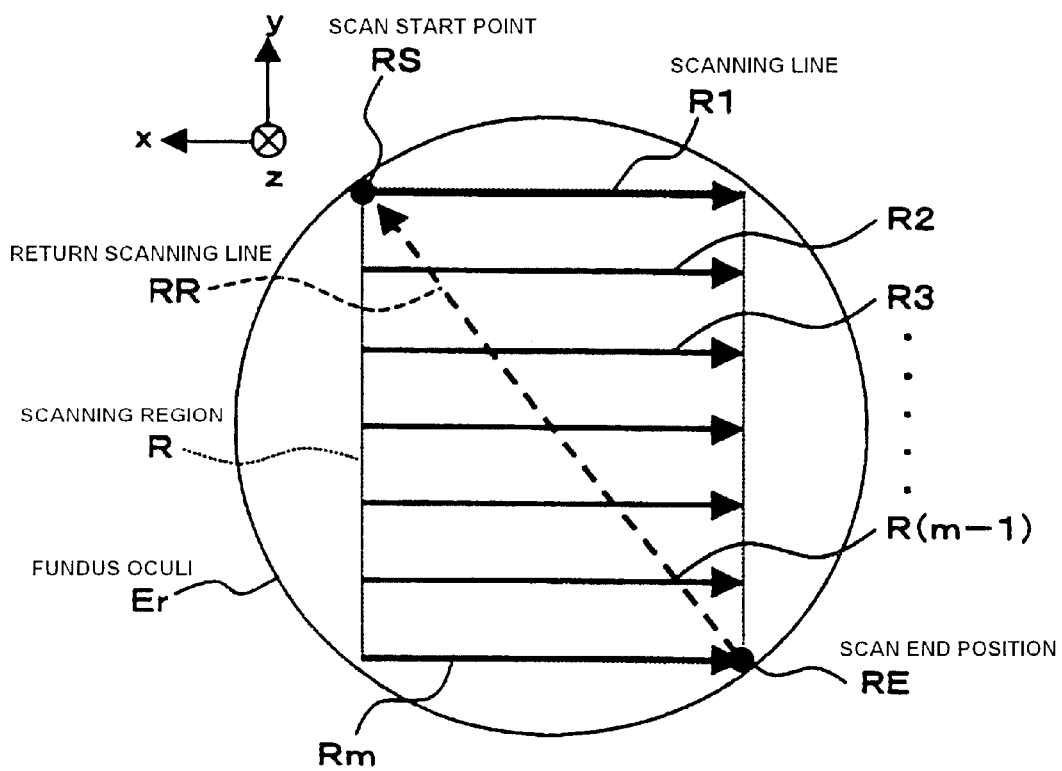
FIG. 5 is a schematic diagram representing one example of the scanning features of a signal light by a preferred embodiment of the optical image measuring device related to the present invention.

Wherein, the image forming part 42 may also form a tomographic image in the direction other than the main scanning direction (the direction of the scanning line Ri; x-direction). In particular, in the present embodiment, the tomographic image of the fundus oculi Er (tomographic image for correction GR in FIG. 6) along a return scanning line RR shown in FIG. 5 is important.

The return scanning line RR corresponds to scanning the incident position (scanning point) of the signal light LS in the direction advancing from a scan end position RE to the scan start point RS. Whereas, the tomographic image for correction GR along the return scanning line RR is used to correct the position of a tomographic image Gi along each scanning line Ri (see FIG. 6) in a tomographic image position correction process described later.

A plurality of (n' number of) scanning points RRk (k=1 through n') are preset on the return scanning line RR similar to the scanning line Ri in FIG. 4. The number of the scanning points on this return scanning point (n') may be the same as or different from the number of the scanning points on each scanning line Ri in the main scanning direction (n). Wherein, it is preferable that the distance between the scanning points on the return scanning line RR (=|RR (K+1)–RRk=; k=1 through n'–1) and the distance between the scanning points on each scanning line Ri (=Ri (j+1)–Rij|; j=1 through n–1) are set to be equal or nearly equal to each other.

Figure 6:
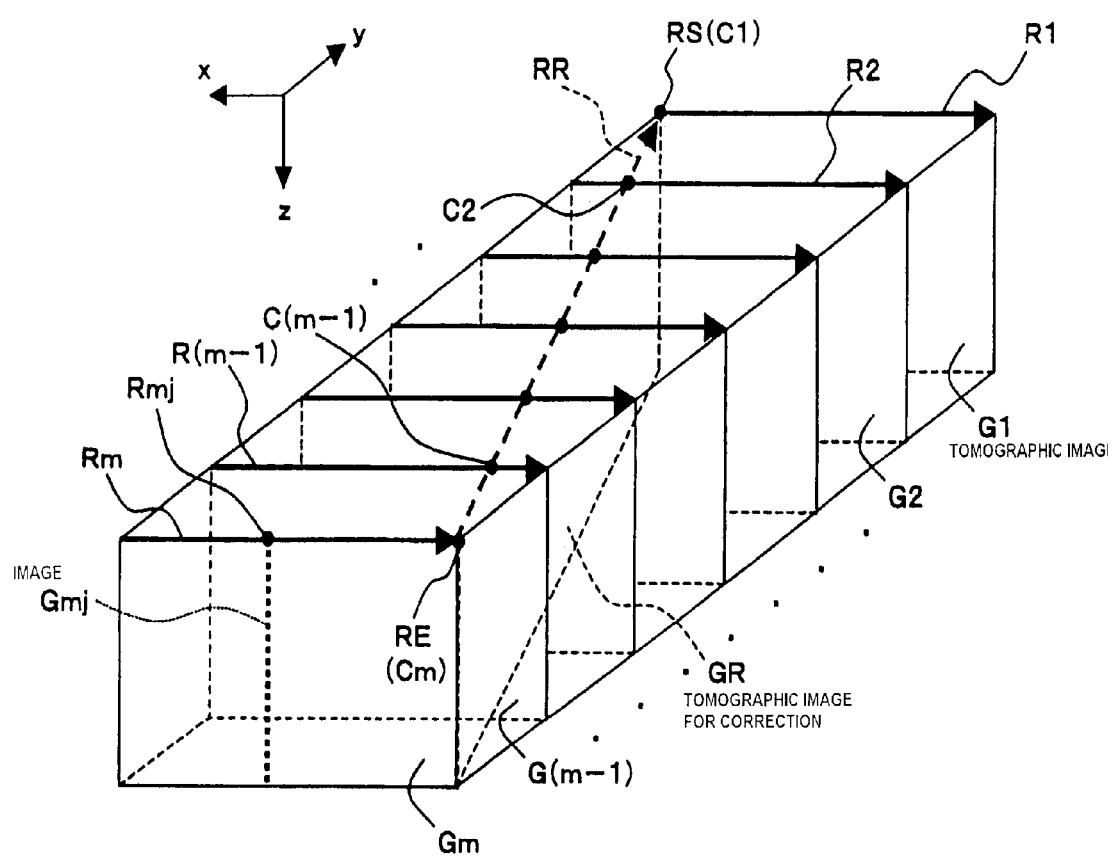
FIG. 6 is a schematic diagram representing one example of the scanning features of a signal light by a preferred embodiment of the optical image measuring device related to the present invention and the form of a tomographic image formed along each scanning line.

As shown in FIG. 6, the return scanning line RR crosses with each scanning line Ri at a crossing position Ci. Wherein, when it is assumed that there is no displacement of the scanning line Ri due to the movement of the eye to be examined E at scanning, the crossing position C1 of the return scanning line RR and the scanning line R1 is the scan start point RS, while the crossing position Cm of the return scanning line RR and the scanning line Rm is the scan end position RE.

Furthermore, the image Gmj in FIG. 6 represents an image in the depth direction (z-direction) at the scanning point Rmj on the scanning line Rm. Likewise, an image in the depth direction at each scanning point Rij on each scanning line Ri formed by the arithmetic process of said first step may be represented as "image Gij." Furthermore, an image in the depth direction at each scanning point RRk on the return scanning line RR may be represented as "image GRk."

Regarding Tomographic Image Position Correction Processing

Figure 7:
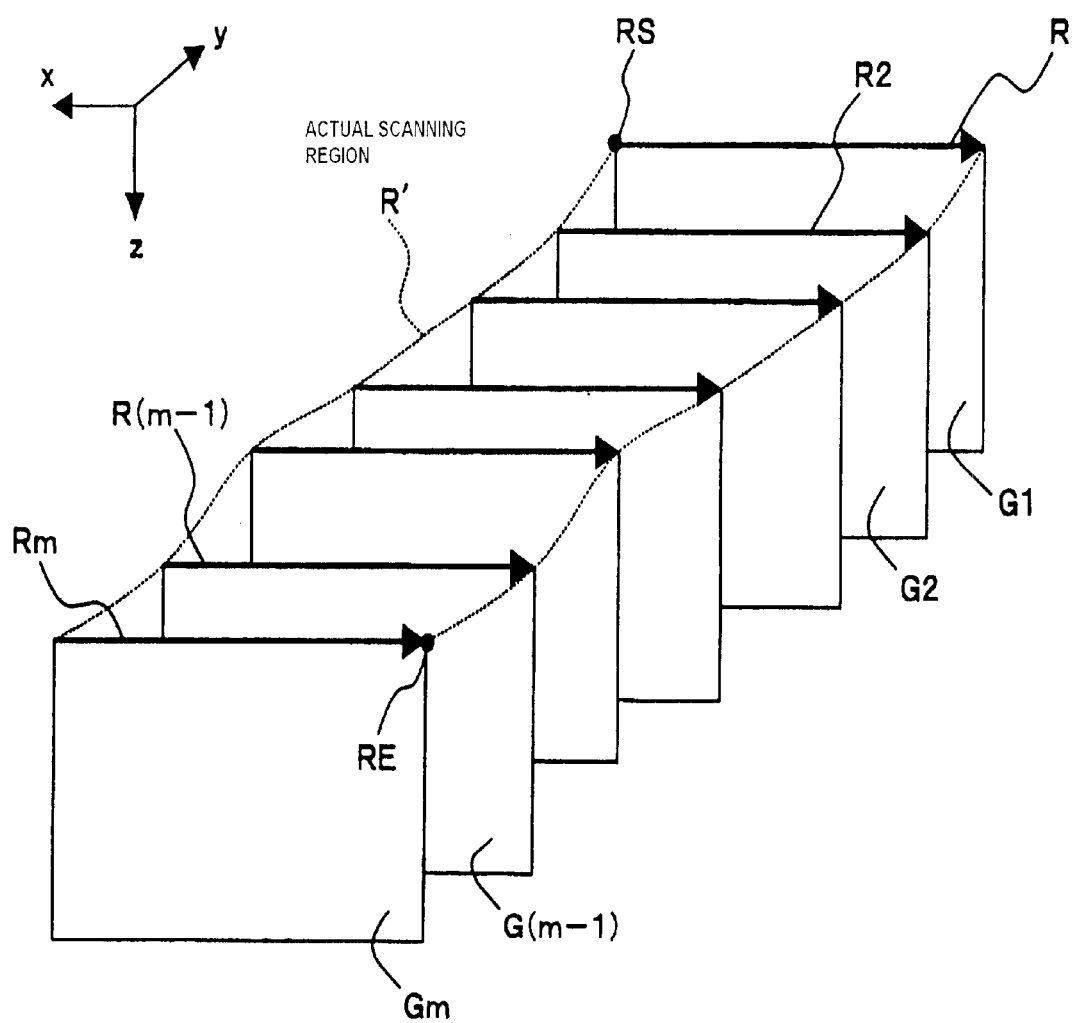
FIG. 7 is a schematic diagram representing one example of an arrangement form of each scanning line and tomographic image when an eye to be examined moves during the scanning of a signal light by a preferred embodiment of the optical image measuring device related to the present invention.

When the eye to be examined E moves during scanning of the signal light LS, the scanning lines R1 to Rm do not make a form in which they are aligned within the rectangular scanning region R shown in FIG. 4 to FIG. 6 and each other's position is displaced as shown in FIG. 7. Then the actual scanning region R' becomes different from the preset scanning region R (see FIG. 4 (A), FIG. 5) and the accuracy of the obtained image deteriorates. In particular, since the eye to be examined E often moves in the z-direction (depth direction) with heartbeat, displacement in the z-direction at the scanning lines R1 to Rm is seen as a problem.

Wherein, when the eye to be examined E moves during scanning along one scanning line Ri, displacement is also generated between the scanning points Rij on this scanning line Ri. In this embodiment, such displacement between scanning points is expressed as "displacement of a scanning line." Wherein, when the eye to be examined E moves during scanning on one scanning line Ri, the scanning line Ri will not be linear as shown in FIG. 4, etc.

The position correction processing part 43 forms a new tomographic image (referred as a tomographic image for comparison) along the return scanning line RR based on a 3-dimensional image of the fundus oculi Er generated with the image forming part 42. Processing to form a tomographic image of arbitrary cross section in a 3-dimensional image can use a method the same as conventional ones.

For example, the position correction processing part 43 forms a tomographic image for comparison as follows:

(1) Set the cross-sectional direction of a 3-dimensional image;

(2) Obtain a crossing position of each tomographic image to become a base (in this example, each of tomographic images G1 to Gm) and the cross-sectional direction;

(3) Obtain an image in the depth direction at the crossing position of each tomographic image; and (4) Form a tomographic image for comparison by connecting images in the depth direction of each tomographic image.

Wherein, in process (4), image processing is to interpolate the interval of images in the depth direction of adjacent tomographic images.

Figure 8:
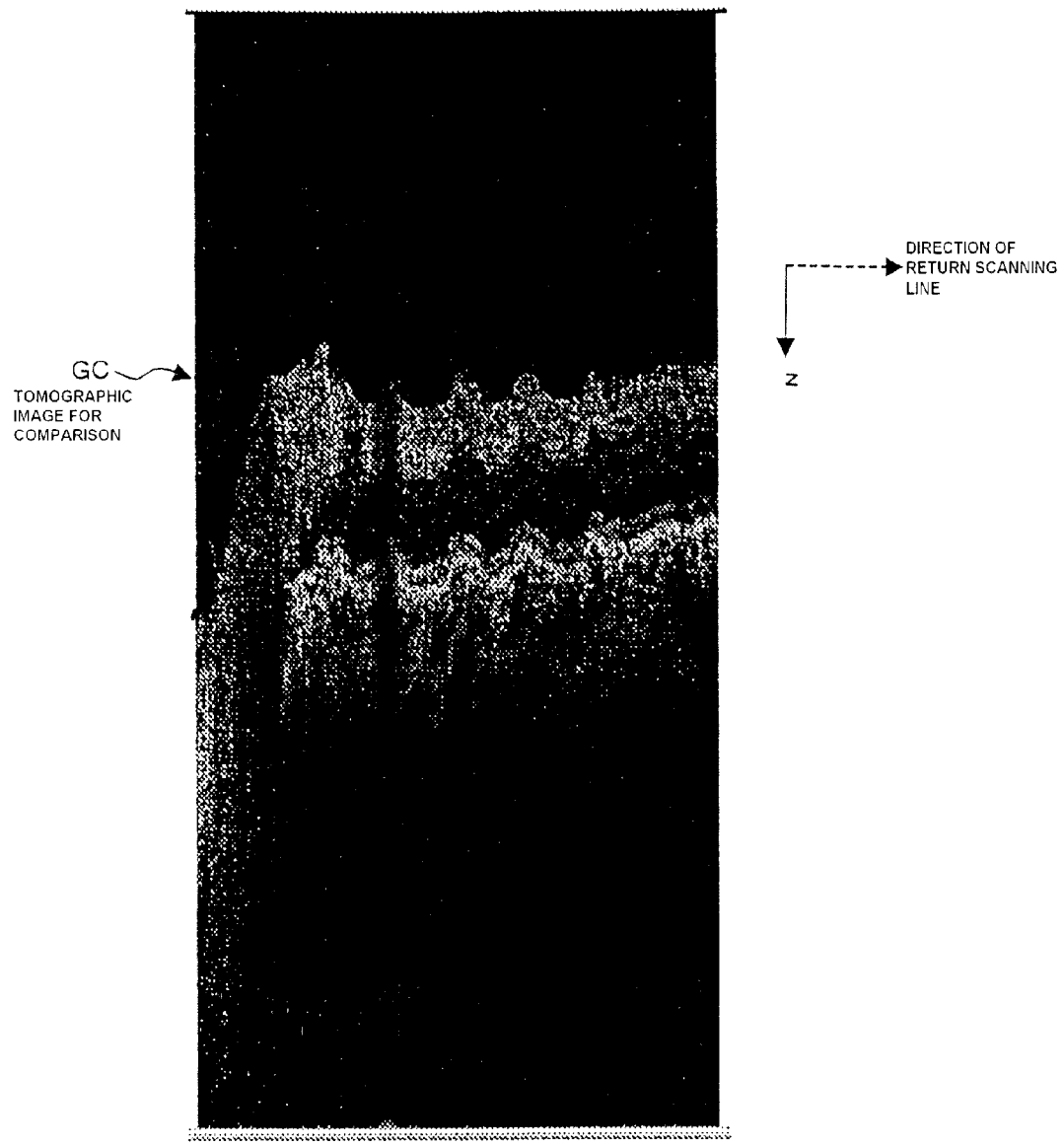
FIG. 8 is a schematic diagram representing one example of a tomographic image for comparison formed by a preferred embodiment of the optical image measuring device related to the present invention.

FIG. 8 represents an example of a tomographic image for comparison formed by the position correction processing part 43 when the position of the scanning lines R1 to Rm is displaced (at least) in the z-direction during scanning. A tomographic image for comparison GC shown in the figure is obtained by measuring a fundus oculi with a relatively smooth surface morphology, in which an image in the depth direction arranged in the return scanning line RR direction is displaced.

Figure 9:
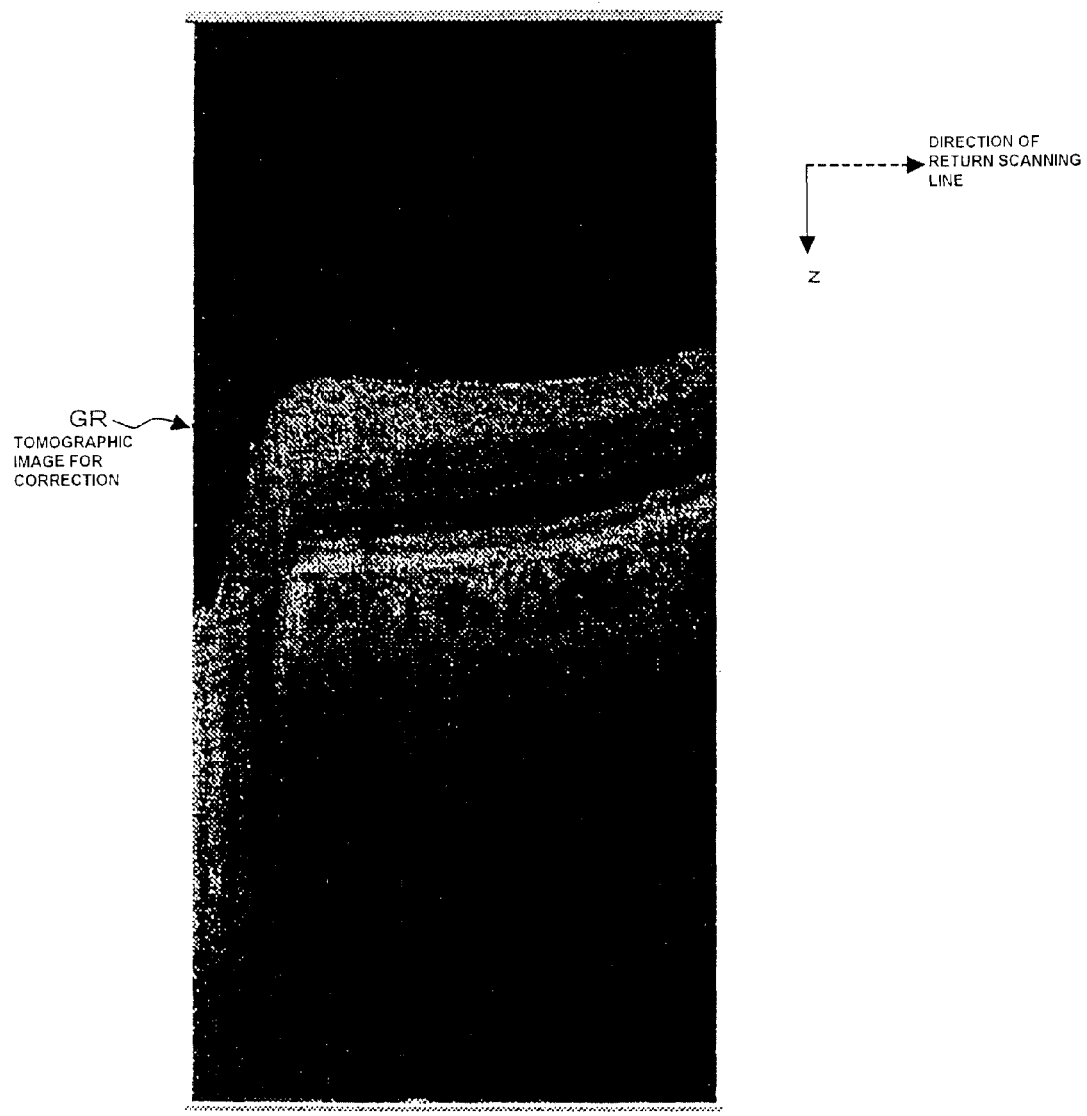
FIG. 9 is a schematic diagram representing one example of a tomographic image for correction formed by a preferred embodiment of the optical image measuring device related to the present invention.

FIG. 9 represents an example of a tomographic image for correction GR obtained for approximately the same fundus oculi as FIG. 8. Since the tomographic image for correction GR is formed based on data (detection signal group) which is obtained at once by linear scanning from the scan end position RE to the scan start point RS, the time required to the scanning is extremely short. Also, in the tomographic image for correction GR shown in FIG. 9, there is little displacement in the z-direction of an image in the depth direction which is arranged in the return scanning line RR direction.

The position correction processing part 43 corrects the position of each tomographic image G1 by comparing such tomographic images for correction GR with the tomographic image for comparison GC. This position correction processing can be performed by employing a method of general image matching such as an aligning (matching) method with a normalized correlation or an image matching method with position matching of the characterizing portion of an image.

However, the method of image matching with the position correction processing part 43 is not limited to these, and any method which may match the position of two images in the relationship of a parallel shift can be applied.

Method with Normalized Correlation

When a method of normalized correlation is used, in terms of an image in the depth direction forming the tomographic image for comparison GC, the position correction processing part 43 sequentially calculates a correlation value of the normalized correlation with an image in the depth direction at a corresponding position of the tomographic image for correction GR while displacing the image in the depth direction every one pixel unit.

Further, it obtains a displacement amount (the number of displaced pixels) $\Delta z_i$ of an image in the depth direction when the value of this correlation value is maximized. This displacement amount $\Delta z_i$ is employed as a correction amount in the z-direction of the tomographic image Gi along the scanning line Ri corresponding to the position of the image in the depth direction (scanning point Rij).

This processing is performed in every image in the depth direction forming the tomographic image for comparison GC. Wherein, when the tomographic image for comparison GC is formed by interpolate processing, it is enough that the processing is performed only for an image in the depth direction corresponding to an intersection point of each scanning line Ri and the return scanning line RR.

Figure 10:
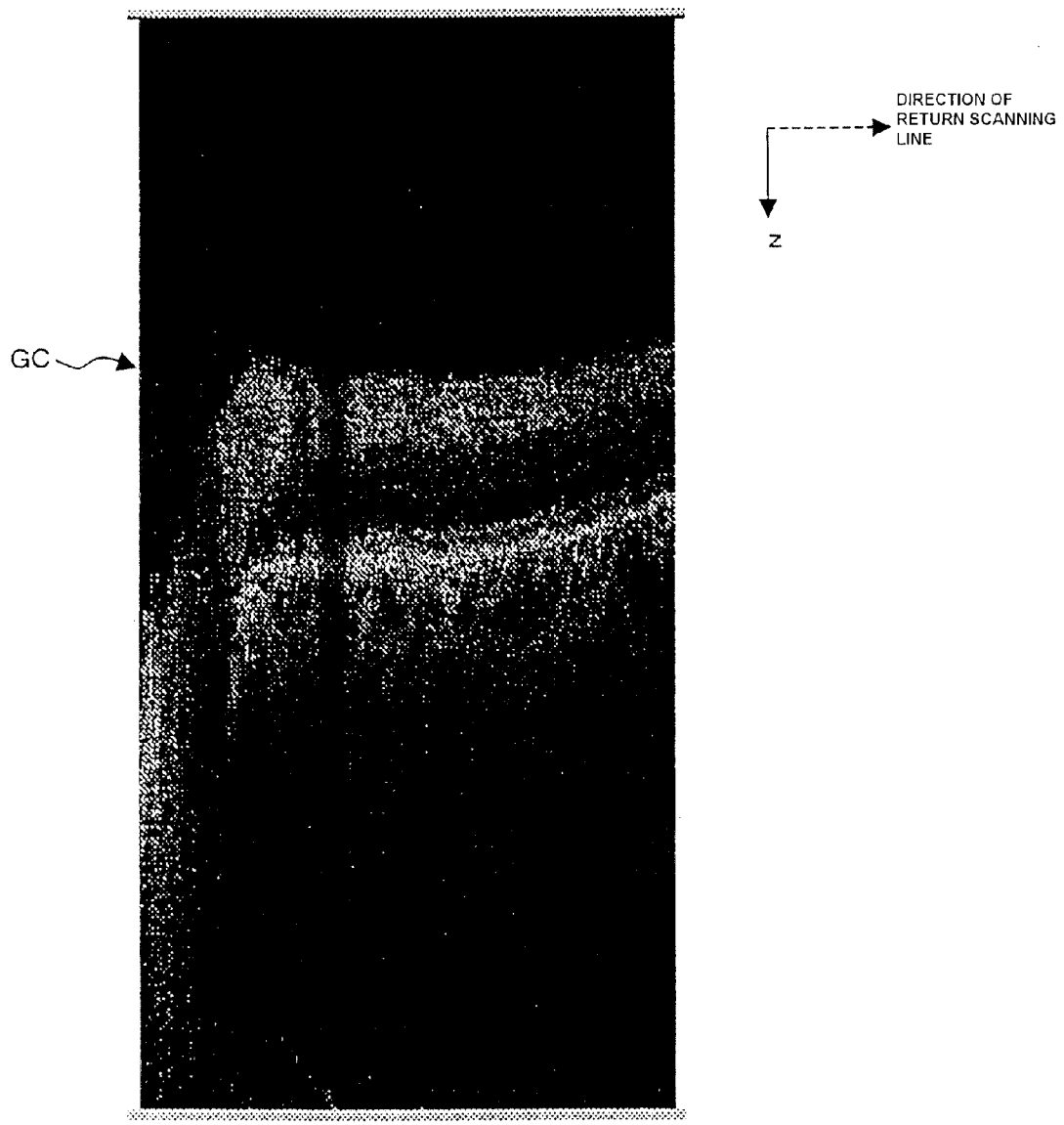
FIG. 10 is a schematic diagram representing one example of a tomographic image for comparison in which the image position is corrected by a preferred embodiment of the optical image measuring device related to the present invention.

FIG. 10 represents a form after correction of the tomographic image for comparison GC when the method with normalized correlation is used for the tomographic image for comparison GC in FIG. 8 and the tomographic image for correction GR in FIG. 9. When this tomographic image for comparison GC in FIG. 10 is compared to FIG. 8, it can be seen that displacement in the z-direction on the image in the depth direction is suitably corrected. Therefore, displacement in the z-direction of the tomographic image Gi of the scanning line corresponding to the position of an image in each depth direction (scanning point Rij) after correction is suitably corrected.

Wherein, although the tomographic image for comparison GC is displaced in the above-mentioned embodiment, it is possible to displace the tomographic image for correction GR. However, in that case, the correction amount by which the symbol of displacement amount $\Delta z_i$ is reversed (that is, $-\Delta z$) is employed as the correction amount of the tomographic image Gi.

Method for Matching the Characterizing Portion

When a method that matches a characterizing portion is used, the position correction processing part 43 extracts a characterizing portion of an image in the depth direction forming the tomographic image for comparison GC and a (same) characterizing portion of an image n the depth direction at a corresponding position of the tomographic image for correction GR.

The characterizing portion of an extraction target is preset with the extraction method. A portion corresponding to the surface of the fundus oculi Er is set as a characterizing portion of an extraction target here. An example of the extraction method is described. The case in which a characterizing portion (a portion corresponding to the surface of a fundus oculi) of the tomographic image for comparison GC shown in FIG. 8 is described. This tomographic image for comparison GC is displayed on a screen of the display 106 of the user interface 44. The display features are configured to display a portion corresponding to the surface of the fundus oculi Er on the upper part of the screen and display a portion corresponding to the deep portion of the fundus oculi Er on the lower part of the screen (see the direction of the z coordinate in FIG. 8).

The pixel value of a background region of the screen in the display 106 is set to zero, and the tomographic image for comparison GC is displayed as a gray-scale image of brightness on this background region (e.g., an image comprising a 256 gray-scale of brightness (pixel value)).

The position correction processing part 43 refers the pixel value of each pixel downward from the upper part to the lower part of the screen for each vertical line of a pixel in a display screen of this tomographic image for comparison GC. Since the pixel value in the background region is zero, "pixel value zero" will continue from the upper part of the screen for a while. It further refers pixel values downward to find a pixel at which the pixel value switches to a positive value from zero.

The coordinate value at which this pixel value becomes a positive value for the first time is stored in a storing device (e.g., RAM 101, hard disk drive 103) of the controlling part 41 as a coordinate value of a part corresponding to the surface of a fundus oculi in the vertical line. Wherein, a coordinate system of a coordinate value of a pixel to be stored may use either the above-mentioned x, y, z coordinate system or a 2-dimensional coordinate system set on a screen.

Wherein, if all pixels to the lowest part of a vertical line are pixel value zero, it is determined that there is no image on the vertical line.

The position correction processing part 43 performs similar processing on each vertical line of a pixel in a display screen of the tomographic image for comparison GC. As a result, a part corresponding to the surface of a fundus oculi in the tomographic image for comparison GC can be extracted.

In addition, the position correction processing part 43 similarly processes the tomographic image for correction GR to extract a part corresponding to the surface of a fundus oculi in the tomographic image for correction GR.

Further, for each vertical line of a pixel on a display screen, the position correction processing part 43 sequentially calculates a correlation value (any correlation value can be used appropriately) with a pixel of a part corresponding to the surface of a fundus oculi of the tomographic image for correction GR while displacing a pixel of a part corresponding to the surface of a fundus oculi of the tomographic image for comparison GC every one pixel unit.

Then, it obtains a displacement amount (the number of displaced pixels) of a pixel when the value of this correlation value is maximized. This displacement amount is employed as a correction amount in the z-direction of the tomographic image Gi along the scanning line Ri corresponding to the vertical line.

Figure 11:
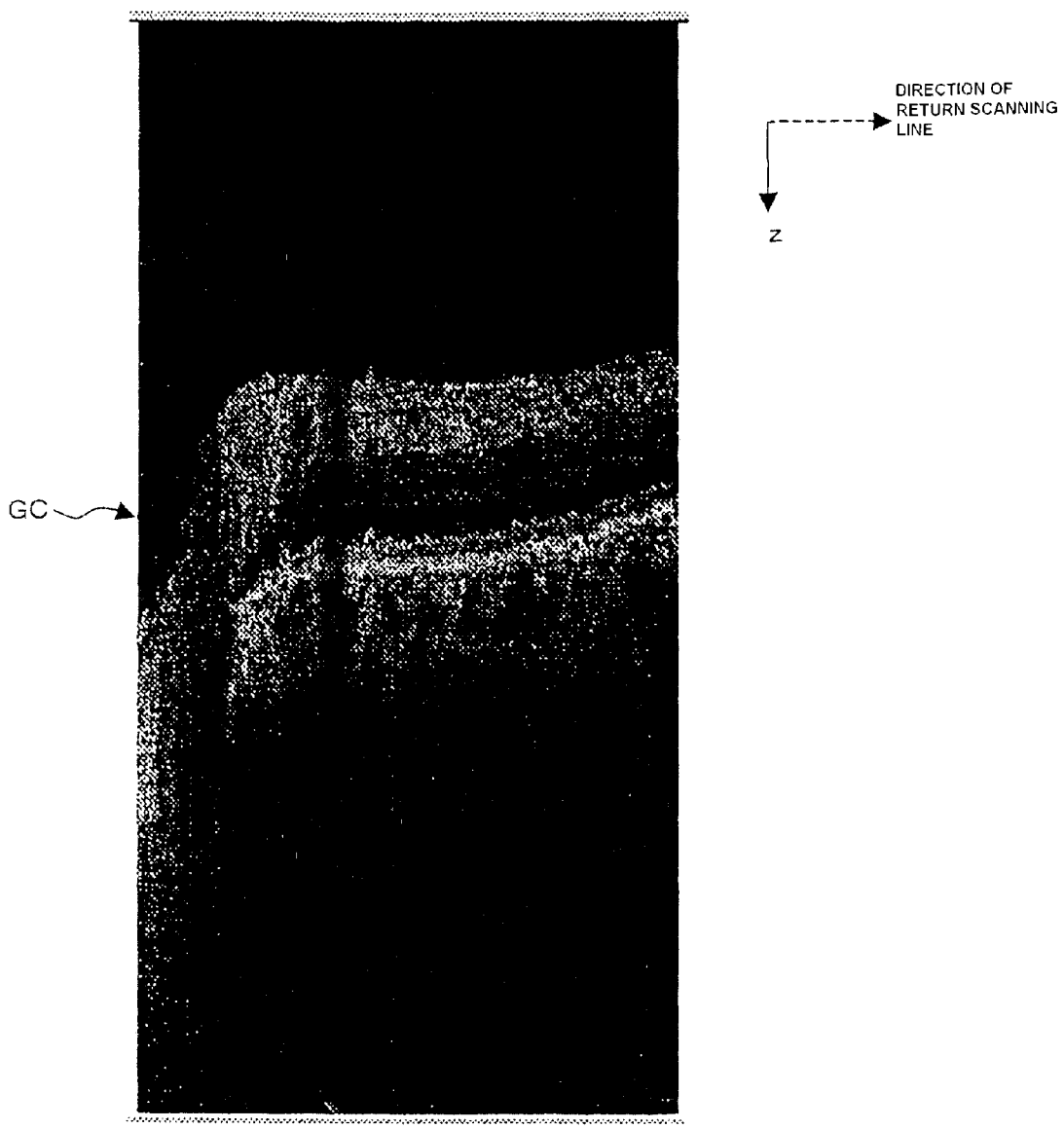
FIG. 11 is a schematic diagram representing one example of a tomographic image for comparison in which the image position is corrected by a preferred embodiment of the optical image measuring device related to the present invention.

FIG. 11 represents a form after correction of the tomographic image for comparison GC when the method to match a part corresponding to the surface of a fundus oculi is used for the tomographic image for comparison GC in FIG. 8 and the tomographic image for correction GR in FIG. 9. When this tomographic image for comparison GC in FIG. 10 is compared to FIG. 8, it is found that the shape of a part corresponding to the surface of a fundus oculi becomes flat and the displacement in the z-direction on the image in the depth direction is suitably corrected. In this way, displacement in the z-direction of the tomographic image Gi of the scanning line corresponding to the position of an image in each depth direction (scanning point Rij) after correction is suitably corrected.

Wherein, although the tomographic image for comparison GC is displaced in the above-mentioned embodiment, it is possible to displace the tomographic image for correction GR. However, in this case, the correction amount by which the symbol of said displacement amount is reversed is employed as the correction amount of the tomographic image Gi.

In addition, a characterizing portion other than a part corresponding to the surface of a fundus oculi can be used. For example, when there is a lesioned part in the tomographic image for comparison GC and the tomographic image for correction GR, the lesioned part can be used as a characterizing portion. As a result, the accuracy of aligning an image of the lesioned part and the peripheral part is improved, and thus, it is expected that the accuracy of views of this lesioned part along with diagnoses will be improved.

Operation

Figure 12:
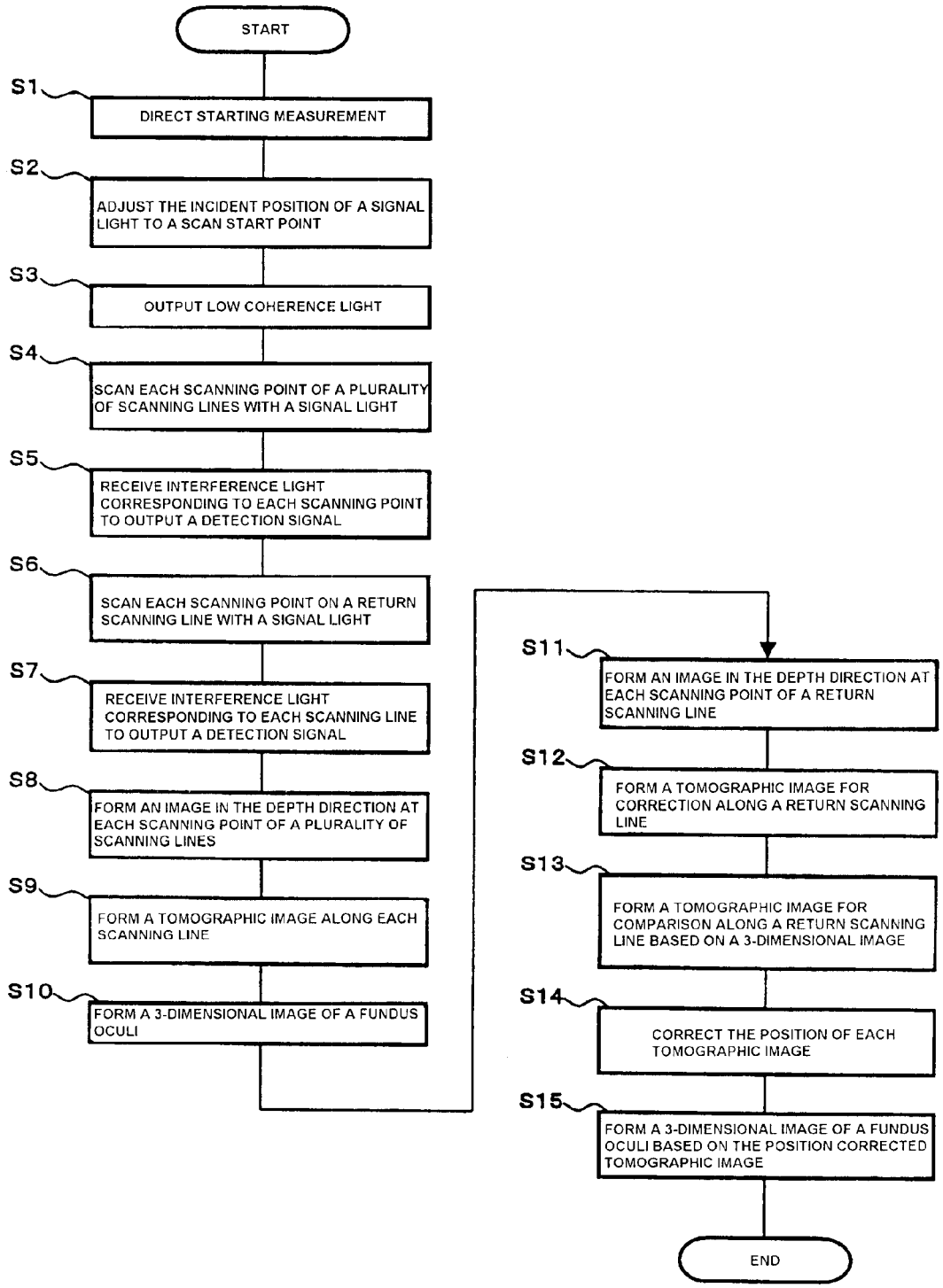
FIG. 12 is a flowchart representing one example of the operational features of a preferred embodiment of the optical image measuring device related to the present invention.

Operation of the optical image measuring device 1 of the present embodiment which is equipped with the above-mentioned constitution is described. The flowchart shown in FIG. 12 represents an example of the operation of the optical image measuring device 1.

When a user operates the user interface 44 of the computer 40 to direct the start of measurement (S1), the controlling part 41 controls the mirror drive mechanisms 22A and 23A to adjust the direction of the Galvanometer mirrors 22 and 23 respectively so that the incident position of the signal light LS is the scan start point RS (S2).

Then, the controlling part 41 controls the low coherence light source 2 to output the low coherence light L0 (S3) and controls the mirror drive mechanisms 22A and 23A to scan each scanning point Rij on a plurality of scanning lines Ri which are set on the fundus oculi Er as shown in FIG. 4 with the signal light LS (S4). The CCD 34 of the spectrometer 30 receives the interference light LC comprising the signal light LS and the reference light LR reflected at each scanning point Rij to output the detection signal Dij (S5).

When scanning is completed to the scan end position RE, the controlling part 41 controls the mirror drive mechanisms 22A and 23A to scan the signal light LS along the return scanning line RR (S6). The CCD 34 receives the interference light LC corresponding to each scanning point RRk on the return scanning line RR to output a detection signal Dk (S7).

The image forming part 42 of the computer 40 forms the image Gij in the depth direction of the fundus oculi Er at the scanning point Rij based on the detecting point Dij corresponding to each scanning point Rij output from step S5 (S8), forms the tomographic image Gi of the fundus oculi Er along each scanning line Ri based on images Gi1 to Gin at the scanning points Ri1 to Rin on each scanning line Ri (S9), and forms a 3-dimensional image of the fundus oculi Er based on the formed tomographic images G1 to Gm (S10).

The image forming part 42 also forms an image GRk in the depth direction of the fundus oculi Er at the scanning point RRk based on the detection signal Dk corresponding to each scanning point RRk on the return scanning line RR output in step S7 (S11), and forms a tomographic image (tomographic image for correction GR) of the fundus oculi Er along the return scanning line RR based on formed images GR1 to GRn' (S12).

Then, the position correction processing part 43 forms the tomographic image for comparison GC along the return scanning line RR based on the 3-dimensional image of the fundus oculi Er formed in step S10 (S13), and corrects the position of each tomographic image G1 to Gm based on this tomographic image for comparison GC and the tomographic image for correction GR formed in step S12 (S14).

The image forming part 42 forms a 3-dimensional image of the fundus oculi Er based on the tomographic images G1 to Gm whose position is corrected (S15).

Action/Effect

According to the above optical image measuring device 1 related to the present embodiment, the following actions and effects are expected.

The optical image measuring device 1 splits the low coherence light L0 output from the low coherence light source 2 into the signal light LS directed toward the eye to be examined E and the reference light LR directed toward the reference mirror 14, generates the interference light LC by overlaying the signal light LS reflected at the fundus oculi Er of the eye to be examined E and the reference light LR reflected at the reference mirror LR, and the CCD 34 which receives this interference light LC outputs a detection signal.

This optical image measuring device 1 also comprises the Galvanometer mirrors 22 and 23 which scan an incident position of the signal light LS for the eye to be examined E in the main scanning direction (x-direction) and the sub-scanning position (y-direction). Further, it comprises the computer 40 (image forming part 42) which forms an image in the depth direction (z-direction) of the fundus oculi Er of the eye to be examined E at the incident position based on a detection signal on the basis of the interference light LC generated from the signal light LS and the reference light LR reflected at the incident position for each of a plurality of incident positions (n number of scanning points Ri1 through Rin; i=1 through m) along the main scanning direction, and forms a tomographic image along the main scanning direction based on an image at this incident position, thereby forming two or more tomographic images (m number of tomographic image Gi; i=1 through m) at difference positions in the sub-scanning direction. The above-mentioned constitution is similar to the conventional optical image measuring device 1.

Characteristics of the present embodiment include that the Galvanometer mirrors 22 and 23 scan the signal light LS in a given direction (direction of return scanning line RR) which crosses the main scanning direction, the image forming part 42 of the computer 40 forms the tomographic image for correction GR along this given direction, and the position correction processing part 43 corrects each displacement of two or more tomographic images (m number of tomographic images Gi; i=1 through m) based on this tomographic image for correction GR.

Wherein, the direction of the tomographic image for correction GR is preset so as to cross all m number of tomographic images. However, even when the position of the eye to be examined E is different at scanning for forming the tomographic image Gi and at scanning for forming the tomographic image for correction GR (that is, the eye to be examined E moves), the tomographic image for correction GR crosses an adjacent region of the tomographic image Gi. Therefore, this tomographic image for correction GR reflects a position of each tomographic image Gi (particularly, positions in the depth direction). It is preferable that the "given direction" of the present invention be a direction crossing all m number of tomographic images Gi.

According to the optical image measuring device 1 related to the present embodiment comprising the above-mentioned characteristics, since displacement of each tomographic image Gi can be corrected using the tomographic image for correction GR along the return scanning line RR even if the object to be measured moves during scanning of a light beam (signal light LS), a highly accurate image can be formed.

Further characteristics of the present embodiment include that the Galvanometer mirror 22 is controlled so as to scan an incident position of the signal light LS in the specified direction of the main scanning direction when the tomographic image Gi is formed, as well as scan an incident position of the signal light along the return scanning line RR advancing from this scanning ending point RE to the starting point RS when the tomographic image for correction GR is formed.

As a result, when scanning for forming the tomographic image Gi is completed, it can quickly shift to scanning for forming the tomographic image for correction GR. Wherein, scanning for forming the tomographic image for correction GR can be performed extremely quickly because it involves scanning with only one scanning line. Therefore, the scanning time with the optical image measuring device 1 is almost the same as conventional ones, and the burden on a subject will not be increased.

Wherein, although it can perform scanning for forming the tomographic image for correction GR before scanning for forming the tomographic image Gi, even in this case, it can quickly shift to scanning for forming the tomographic image Gi after completing scanning for forming tomographic image for correction GR.

The optical image measuring device 1 related to the present embodiment corrects displacement in the depth direction (z-direction) of each of m number of tomographic images Gi. Displacement in the depth direction is caused by the change in bloodstream with the heartbeat of a heart and by subjects moving their head back and forth; however, in the present embodiment, such displacement can be preferably corrected.

In addition, for each tomographic image Gi, the optical image measuring device 1 related to the present embodiment corrects displacement in the depth direction of the tomographic image Gi by matching a position of an image in the depth direction at the crossing position Ci with the tomographic image for correction GR with a position of an image in the depth direction of the tomographic image for correction GR at this crossing position Ci. The tomographic image for correction GR reflects a position in the depth direction of each tomographic image Gi as described above. As a result, according to the present embodiment, a position in the depth direction of each tomographic image Gi can be suitably corrected based on this tomographic image for correction GR.

The correction of displacement in the depth direction of each tomographic image Gi with the optical image measuring device 1 related to the present embodiment is performed by shifting the tomographic image Gi in the depth direction so that the correlation value of normalized correlation between an image in the depth direction of the tomographic image Gi at the crossing position Ci and an image in the depth direction of the tomographic image for correction GR is maximized. Therefore, displacement of each tomographic image Gi can be corrected with high accuracy.

As another example of displacement correction in the depth direction of each tomographic image Gi, the tomographic image Gi can be shifted so as to match a characterizing portion of an image in the depth direction of the tomographic image Gi at the crossing position Ci with a characterizing portion of an image in the depth direction of the tomographic image for correction GR. This characterizing portion is considered to be a portion, for example, corresponding to the surface of the fundus oculi Er of each image Gi and GR. By such correction processing, displacement of each tomographic image Gi can be corrected with high accuracy.

The optical image measuring device 1 related to the present embodiment is configured to form a 3-dimensional image of the fundus oculi Er based on m number of the tomographic images Gi, form the tomographic image for comparison GC along a given direction (direction of return scanning line RR) based on this 3-dimensional image, and correct displacement of each tomographic image Gi based on displacement of the tomographic image for comparison GC to the tomographic image for correction GR. Displacement of each tomographic image Gi can be obtained with high accuracy by using such tomographic images for comparison GC.

Modified Example

The constitution described above is only one example to preferably implement the present invention. Any modification as described below can be implemented appropriately within the scope of the invention.

The tomographic image for correction is not limited to the tomographic image for correction GR in said embodiment. The tomographic image for correction related to the present invention is sufficient to cross all tomographic images which are targeted by displacement correction.

In addition, the tomographic image for correction may not only consist of a single plane like the above-mentioned embodiment, but may consist of a plurality of planes or a curved surface with appropriate control of the Galvanometer mirrors 22 and 23.

A method for displacement correction of a tomographic image is not limited to a method of normalized correlation and a method to match a characterizing portion as described in the above embodiment, but any method which may correct at least parallel shifting of a tomographic image may be applied.

In addition, as in the above embodiment, a method can be used other than the method in which a 3-dimensional image is formed from two or more tomographic images, a tomographic image for comparison that is a cross-section of the 3-dimensional image, and displacement of the tomographic image is corrected based on displacement of the tomographic image for comparison with respect to the tomographic image for correction. For example, regarding each of two or more tomographic images, by setting both scanning points of the tomographic images and the tomographic image for comparison at the crossing position thereof, and by comparing both images in the depth direction at the scanning points, displacement of that tomographic image can be corrected.

In addition, correction of tomographic images can be performed not only in the depth direction (z-direction) but also in the x-direction and y-direction. Hereinafter, one example of the correction method for that purpose is explained.

A suitably sized near-field region is preset for the crossing position of each tomographic image and tomographic image for correction. The near-field region can be set, for example, in a circle with a given radius centered on that crossing position.

A 3-dimensional image in the depth direction for which the surface is the near-field region (in the above example, it is a cylindrical image) is extracted from 3-dimensional images formed from two or more tomographic images. Next, the one with the highest degree of matching to the tomographic image for correction with respect to the image in the depth direction at that crossing position is selected from images in the depth direction at each point within said near-field region. For determination of the degree of matching, for example, conventional methods such as the normalized correlation described above can be used.

The x coordinate and y coordinate of the selected image in the depth direction are obtained, and displacement of that crossing position from the x coordinate and y coordinate are calculated respectively. Since the displacement expresses displacement of that tomographic image in the x-direction and y-direction, these are used to correct displacement of that tomographic image.

In the above embodiment, human fundus oculi is applied as an object to be measured but the present invention can be applied to any site of a living body (limited to sites that can be measured by an optical image measuring device).

In addition, in the above embodiment, an optical image measuring device configured to measure the surface and internal morphology of the object to be measured using the reflection light by the object to be measured have been explained; however, the present invention can also be applied to an optical image measuring device configured to measure the surface and internal morphology thereof using the light penetrating the object to be measured.

Embodiment 2

Next, one example of the preferred embodiments of a fundus observation device and fundus observation program related to the present invention is described.

Figure 13:
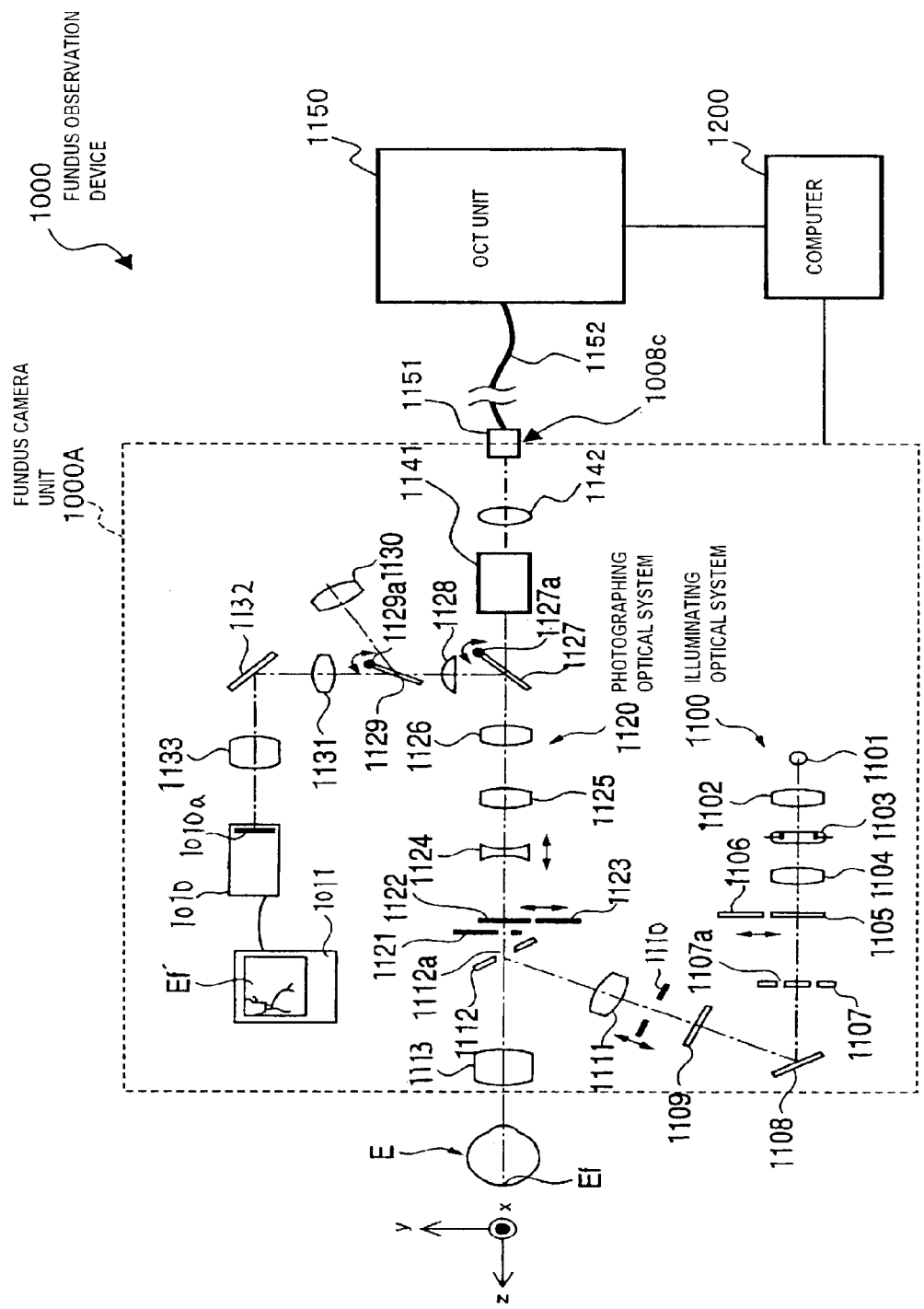
FIG. 13 is a schematic diagram representing one example of the entire constitution of a preferred embodiment of the fundus observation device related to the present invention.
Figure 14:
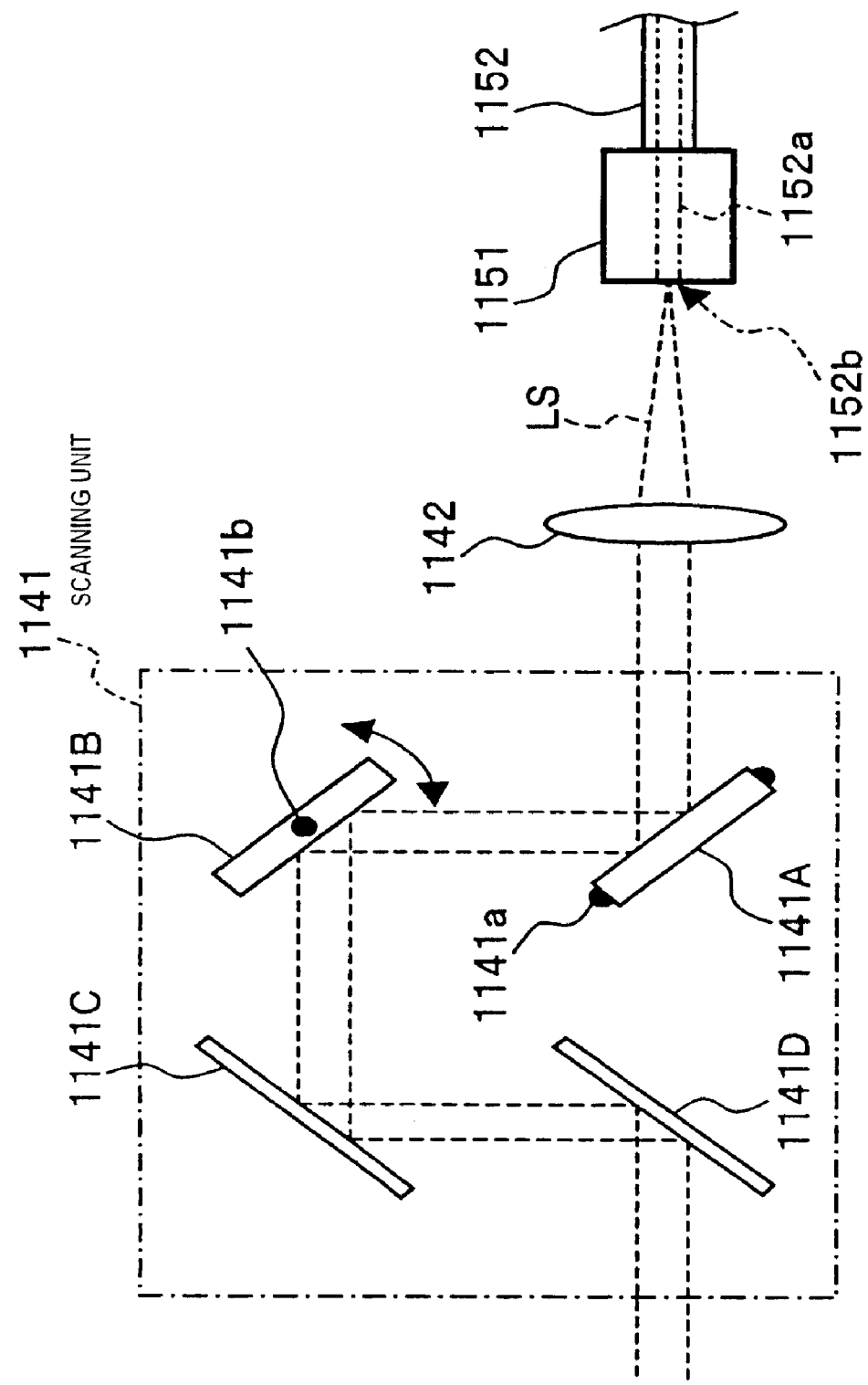
FIG. 14 is a schematic block diagram representing one example of the composition of a scanning unit embedded in a fundus oculi camera unit in a preferred embodiment of the fundus observation device related to the present invention.
Figure 15:
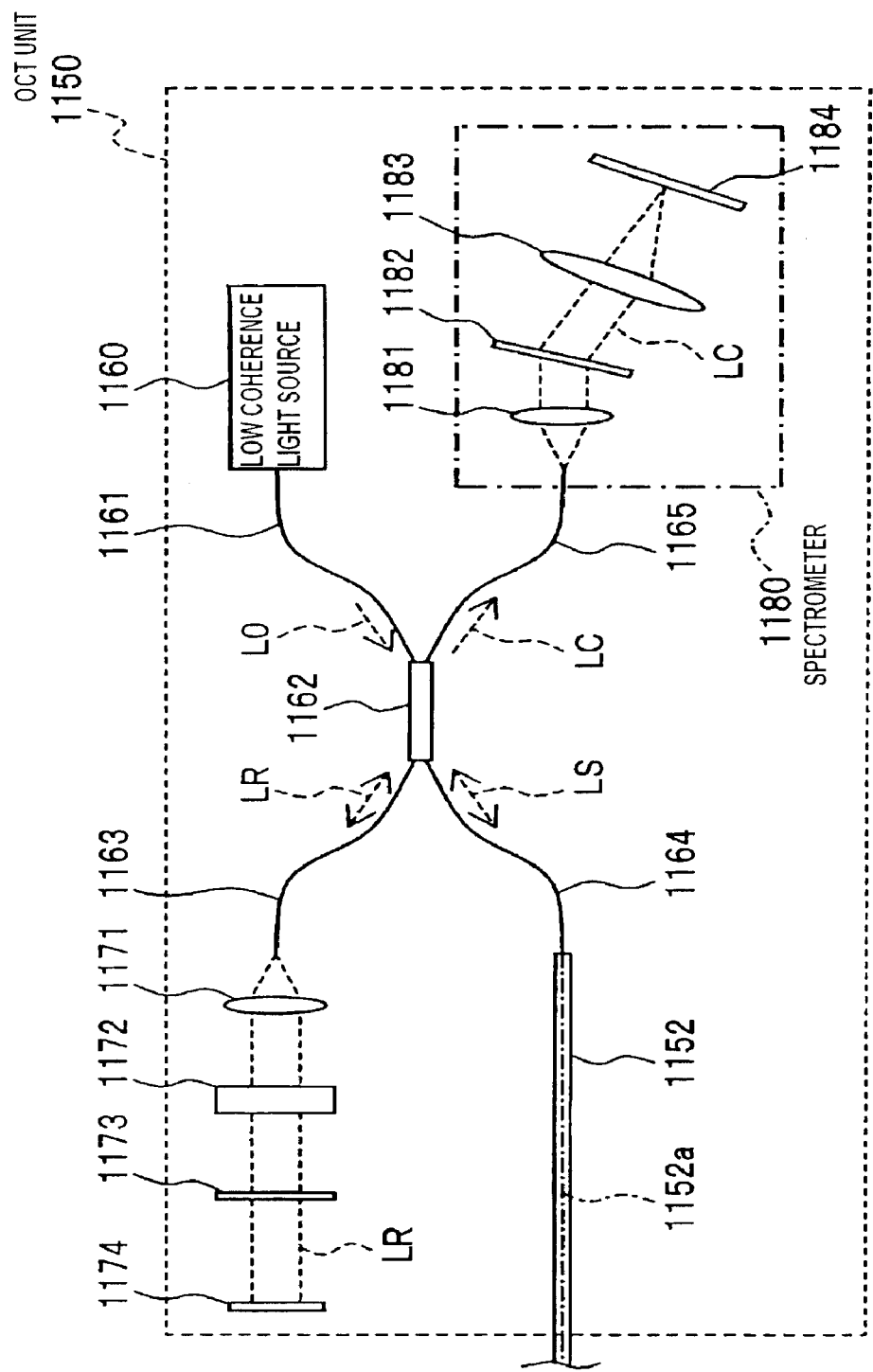
FIG. 15 is a schematic diagram representing one compositional example of an OCT unit in a preferred embodiment of the fundus observation device related to the present invention.
Figure 16:
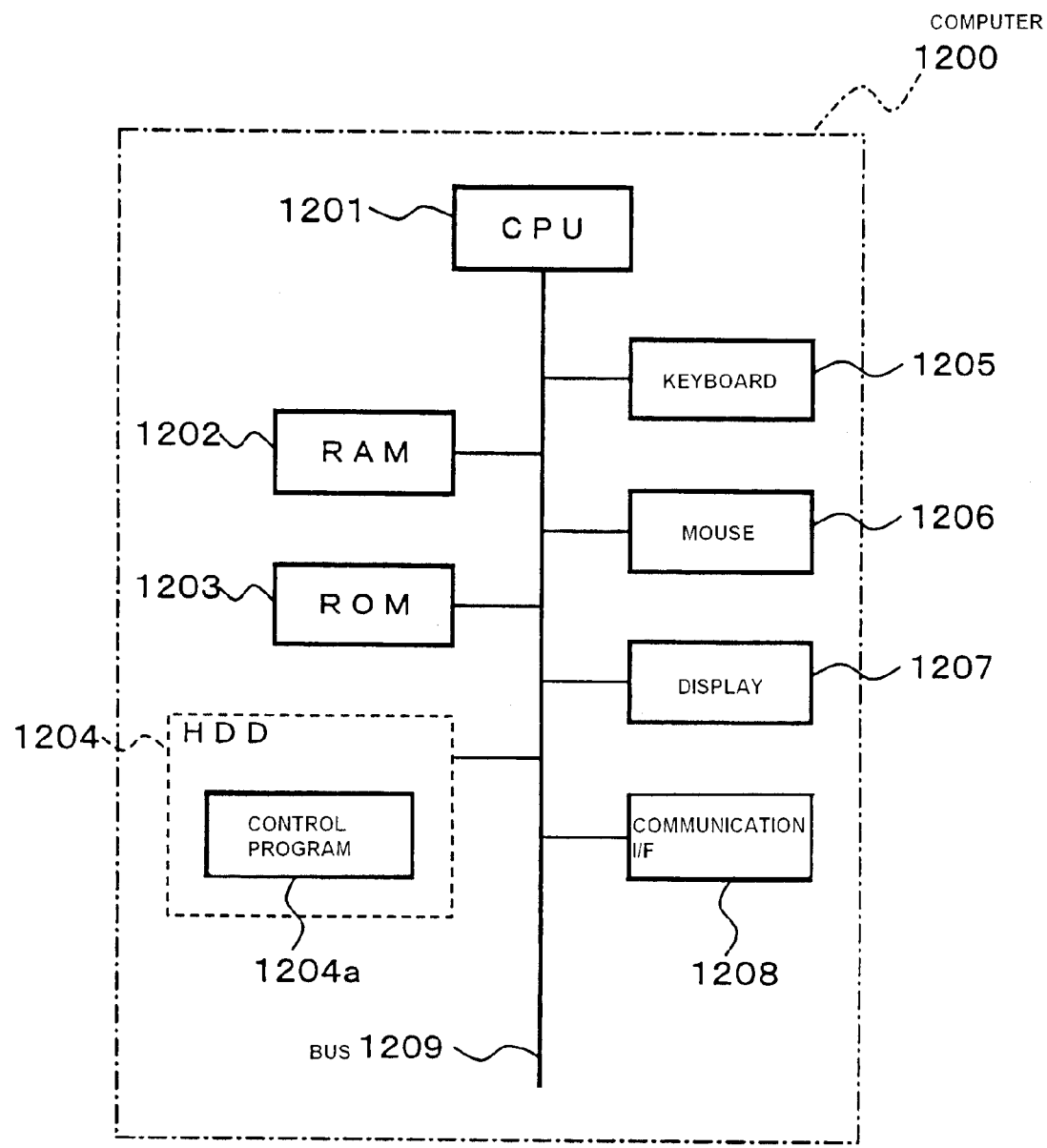
FIG. 16 is a schematic block diagram representing one example of hardware configurations of a computer in a preferred embodiment of the fundus observation device related to the present invention.
Figure 17:
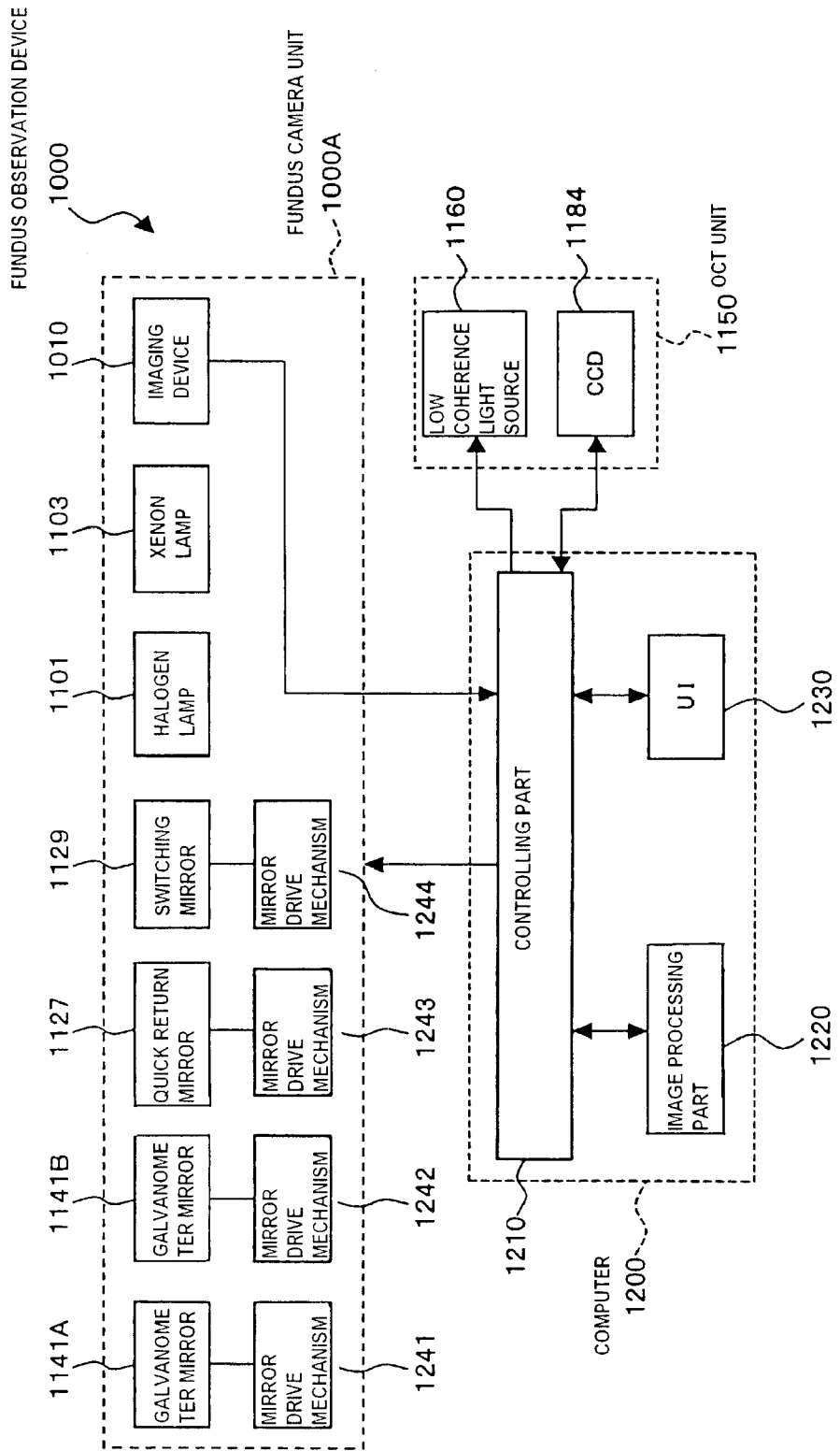
FIG. 17 is a schematic block diagram representing one compositional example of a control system in a preferred embodiment of the fundus observation device related to the present invention.

First, the constitution of the fundus observation device of the present embodiment is explained referring to FIGS. 13 to 17. FIG. 13 shows the entire constitution of a fundus observation device 1000 related to the present embodiment. FIG. 14 shows the constitution of a scan unit 1141 in the fundus camera unit 1000A. FIG. 15 shows the constitution of an OCT unit 1150. FIG. 16 shows the hardware configuration of a computer 1200. FIG. 17 shows the constitution of a control system of the fundus observation device 1000.

Entire Constitution

As shown in FIG. 13, the fundus observation device 1000 is comprised of a fundus camera unit 1000A that functions as a fundus camera, an OCT unit 1150 accommodating the optical system of an optical image measuring device (OCT device), and a computer 1200 that executes various control processes, etc.

This fundus camera unit 1000A is the equivalent of one example of the "first image forming means" of the present invention. In addition, the OCT unit 1150 and the (image processing part 1220 of the) computer 1200 are the equivalent of one example of the "second image forming means" of the present invention. In addition, this "second image forming means" also includes a scan unit 1141 provided in the fundus camera unit 1000A.

To the OCT unit 1150, one end of a connection line 1152 is attached. To the other end of this connection line 1152, a connector part 1151 is attached. This connector part 1151 is attached to a mounting part 1008c formed in the chassis of the fundus camera unit 1000A. Furthermore, a conductive optical fiber runs through the inside of the connection line 1152. The OCT unit 1150 and the fundus camera unit 1000A are optically connected through the connection line 1152. The composition details of the OCT unit 1150 are to be described later referring to FIG. 15.

Constitution of a Fundus Camera Unit

The fundus camera unit 1000A has substantially the same appearance as conventional fundus cameras. Furthermore, as in the optical system of conventional fundus cameras, the fundus camera unit 1000A is provided with an illuminating optical system 1100 to light a fundus oculi Ef of an eye to be examined E, and a photographing optical system 1120 for guiding the fundus reflection light of the illumination light to an eyepiece (not shown), an imaging device 1010, and an OCT unit 1150.

Also, the illuminating optical system 1100 is comprised as in conventional ones including: a halogen lamp 1101, a capacitor lens 1102, a xenon lamp 1103, a capacitor lens 1104, an exciter filter 1105 and 1106, a ring transparent plate 1107, a mirror 1108, a liquid crystal display 1109, an illumination diaphragm 1110, a relay lens 1111, an aperture mirror 1112, and an objective lens 1113.

Also, as in conventional ones, the photographing optical system 1120 comprises: an objective lens 1113, an aperture mirror 1112 (aperture part 1112a thereof), a photographing diaphragm 1121, a barrier filter 1122 and 1123, a variable magnifying lens 1124, a relay lens 1125, a photographing lens 1126, a quick return mirror 1127, a field lens (eye vision lens) 1128, a switching mirror 1129, an eyepiece 1130, a relay lens 1131, a reflection mirror 1132, a photographing lens 1133 and an image pick-up element 1010a.

The image pick-up element 1010a is an image pick-up element such as CCD, etc. installed internally in the imaging device 1010 such as a TV camera. A 2-dimensional image (fundus oculi image Ef) of the surface of a fundus oculi Ef photographed by the imaging device 1010 is displayed on display devices such as on the touch panel monitor 1011, or on a display (to be described later) of the computer 1200.

Furthermore, the photographing optical system 1120 of the present embodiment is provided with a scanning unit 1141 and a lens 1142. The scanning unit 1141 is equipped with a constitution to scan the light output (signal light LS; to be described later) from the OCT unit 1150 on a fundus oculi Ef.

The lens 1142 incidents the signal light LS from the OCT unit 1150 in the form of parallel light flux onto the scanning unit 1141. Furthermore, the lens 1142 acts so as to converge the fundus reflection light of the signal light LS that has reached through the scanning unit 1141.

In FIG. 14, one example of a concrete composition of the scanning unit 1141 is shown. The scanning unit 1141 is comprised including Galvanometer mirrors 1141A, 1141B, and reflection mirrors 1141C, 141D.

The Galvanometer mirrors 1141A and 1141B are to be rotatable centering around rotary shafts 1141a and 1141b respectively. The rotary shaft 1141a and 1141b are arranged perpendicular to each other. In FIG. 14, the rotary shaft 1141a of the Galvanometer mirror 1141A is arranged parallel to the page on the same figure, while the rotary shaft 1141b of the Galvanometer mirror 1141B is arranged perpendicular to the page in the same figure. That is, the Galvanometer mirror 1141B is to be rotatable in the directions indicated by the double-headed arrow in FIG. 14, while the Galvanometer mirror 1141A is to be rotatable in the directions perpendicular to the double-headed arrow. As a result, this pair of Galvanometer mirrors 1141A and 1141B act so that the reflecting direction of the signal light LS changes in a direction perpendicular to each other. Furthermore, the rotary movement of the Galvanometer mirrors 1141A and 1141B respectively is driven by a drive mechanism to be described later.

The signal light LS reflected by the Galvanometer mirrors 1141A and 1141B is to be reflected by reflection mirrors 1141C and 1141D, and is to advance in the same direction as having entered into the Galvanometer mirror 1141A.

As described previously, a conductive optical fiber 1152a runs inside the connection line 1152, and the end face 1152b of the optical fiber 1152a is arranged opposing the lens 1142. The signal light LS emitted from this end face 1152b advances while gradually expanding its beam diameter toward the lens 1142 until being converged to a parallel light flux by this lens 1142. In contrast, the fundus reflection light of the signal light LS is converged toward the end face 1152b by this lens 1142.

Constitution of OCT Unit

Next, referring to FIG. 15, the constitution of the OCT unit 1150 is described. The OCT unit 1150 shown in the same figure has substantially the same optical system as a conventional optical image measuring device and is equipped with an interferometer that splits the light output from a light source into reference light and signal light, and generates interference light by the reference light that has passed through a reference object and the signal light that has passed through an object to be measured (fundus oculi Ef), and at the same time, is configured to form images of the object to be measured by analyzing the detection results of this interference light.

A low coherence light source 1160 is composed of a broad band light source such as super luminescent diode (SLD) that outputs low coherence light L0 or a light emitting diode (LED), etc. This low coherence light L0, for instance, has a wavelength in the near-infrared region and is supposed to be light having a time-wise coherence length of approximately several tens of micrometers.

The low coherence light L0 output from the low coherence light source 1160 is guided to an optical (coupler) 1162 through an optical fiber 1161 composed of, for example, a single mode fiber, and then split into reference light LR and signal light LS.

Furthermore, the optical coupler 1162 has both actions, i.e., a means for splitting the light (splitter) and a means for overlaying the light (coupler); however, herein it is conventionally referred to as an "optical coupler."

The reference light LR is guided by an optical fiber 1163 and emitted from the end face of the fiber. The emitted reference light LR is reflected by a reference mirror 1174 (reference object) through a glass block 1172 and a density filter 1173 after having been converged into a parallel light flux by a collimator lens 1171.

The reference light LR reflected by the reference mirror 1174 is converged to the end face of the fiber of the optical fiber 1163 by the collimator lens 1171 again through the density filter 1173 and the glass block 1172. The converged reference light LR is guided to the optical coupler 1162 through the optical fiber 1163.

Furthermore, the glass block 1172 and the density filter 1173 act as a delaying means to match the optical path length (optical distance) between the reference light LR and the signal light LS, and as a means to match the dispersion characteristics of the reference light LR and the signal light LS.

Whereas, the signal light LS is guided to the end part of the connection line 1152 by an optical fiber 1164. A conductive optical fiber 1152a runs inside the connection line 1152. Herein, the optical fiber 1164 and the optical fiber 1152a may be composed of a single optical fiber or may be jointly formed by connecting each end. In either case, it is sufficient as long as the optical fiber 1164 and 1152a are composed so as to be capable of transferring the signal light LS between the fundus camera unit 1000A and the OCT unit 1150.

The signal light LS is guided within the connection line 1152 to the fundus camera unit 1000A. Then, the signal light LS enters the eye to be examined E through the lens 1142, the scanning unit 1141, the photographing lens 1126, the relay lens 1125, the variable magnifying lens 1124, the photographing diaphragm 1121, the aperture part 1112a of an aperture mirror 1112, and the objective lens 1113 (then, as described later, the barrier filter 1122 and 1123 as well as the quick return mirror 1127 are retracted from the optical path respectively).

The signal light LS that has entered the eye to be examined E forms an image on a fundus oculi (retina) Ef and is then reflected. Then, the signal light LS is not only reflected on the surface of the fundus oculi Ef, but is also scattered at the refractive index boundary reaching the deep region of the fundus oculi Ef. As a result, the fundus reflection light of the signal light LS becomes light containing the information reflecting the surface state of the fundus oculi Ef and the information reflecting the scattered state in the rear at the refractive index boundary of the deep area tissue. The light is simply referred as fundus reflection light (signal light LS thereof).

The fundus reflection light of the signal light LS advances reversely on the above route and converges at the end face 1152b of the optical fiber 1152a, then enters the OCT unit 1150 through this optical fiber 1152, and returns to the optical coupler 1162 through the optical fiber 1164. The optical coupler 1162 overlays this signal light LS and the reference light LR reflected at the reference mirror 1174 to generate interference light LC. The generated interference light LC is guided into a spectrometer 1180 through an optical fiber 1165.

Herein, the "interference light generating means" in the present invention is comprised of an interferometer including at least an optical coupler 1162, an optical fiber 1163 and 1164, and a reference mirror 1174. Furthermore, although a Michelson type interferometer has been adopted in the present embodiment, for instance, a Mach Zender type, etc. or any optional type of interferometer may be adopted appropriately.

The spectrometer 1180 is comprised of a collimator lens 1181, a diffraction grating 1182, an image forming lens 1183, and a CCD (Charge Coupled Device) 1184. The diffraction grating 1182 in the present embodiment is a transmission type diffraction grating; however, needless to say, a reflection type diffraction grating may also be used. Furthermore, needless to say, in place of the CCD 1184, it is also possible to adopt other photo-detecting elements (detecting means).

The interference light LC entering the spectrometer 1180 is split (spectral resolution) by the diffraction grating 1182 after having been converged into a parallel light flux by the collimator lens 1181. The split interference light LC forms an image on the image pick-up surface of the CCD 1184 by the image forming lens 1183. The CCD 1184 receives this interference light LC that is to be converted to an electrical detection signal, and outputs this detection signal to the computer 1200.

Computer Configuration

Next, the configuration of the computer 1200 is described referring to FIG. 16. This computer 1200 analyzes the detection signal input from the CCD 1184 and forms tomographic images of a fundus oculi Ef of an eye to be examined E. The analysis technique is the same technique as the conventional Fourier domain OCT technique. Furthermore, the computer 1200 executes control of each part of the fundus camera unit 1000A and control of each part of the OCT unit 1150.

The fundus camera unit 1000A is controlled by, for example: controlling the output of illumination light by the halogen lamp 1101 or the xenon lamp 1103; controlling the insertion/retraction operation of the exciter filters 1105, 1106, or the barrier filters 1122, 1123 on the optical path; controlling the display operation of the liquid crystal display 1109; controlling the shift of the illumination diaphragm 1110 (controlling the diaphragm value); controlling the diaphragm value of the photographing diaphragm 1121; controlling the shift of the variable magnifying lens 1124 (controlling the magnification); controlling the insertion/retraction operation of the quick return mirror 1127 or the switching mirror 1129 on the optical path (switching the optical path), etc. Furthermore, the computer 1200 controls the rotary operations of the Galvanometer mirrors 1141A, 1141B within the scanning unit 1141.

Whereas, regarding control of the OCT unit 1150, output control of the low coherence light by a low coherence light source 1160 or control of accumulated time of the CCD 1184, etc. is performed.

The hardware configuration of the computer 1200 that acts as described above is explained referring to FIG. 16. The computer 1200 is provided with a hardware configuration that is the same as conventional computers. More specifically, the configuration includes: a CPU 1201 (a type of microprocessor), a RAM 1202, a ROM 1203, a hard disk drive (HDD) 1204, a key board 1205, a mouse 1206, a display 1207, and a communication interface (I/F) 1208. Each part is connected through a bus 1209.

The CPU 1201 executes operations characteristic of the present invention by rolling out a control program 1204a that has been stored in the hard disk drive 1204, on the RAM 1202. This control program 1204a is the equivalent of one example of the "fundus observation program" in the present invention.

Furthermore, the CPU 1201 controls each part of the devices that have previously been described, various arithmetic processes, etc. Moreover, it controls each part of the devices that respond to an operation signal from the key board 1205 or the mouse 1206, controls the display processes by the display 1207, and controls the transmitting/receiving processes of various types of data or controls signals, etc. by the communication interface 1208.

The keyboard 1205, the mouse 1206 and the display 1207 are used as a user interface of the fundus observation device 1000. The keyboard 1205 is used as a device for entering letters or figures, etc. by typing. The mouse 1206 is used as a device to perform various entry operations with respect to the display screen of the display 1207.

Furthermore, the display 1207, an optional display device such as LCD (Liquid Crystal Display) or CRT (Cathode Ray Tube), etc., displays images of a fundus oculi Ef formed by the fundus observation device 1000 and displays various operation screens or set up screens, etc.

Furthermore, the user interface of the fundus observation device 1000 is not limited to such a configuration but may be configured by using an optional user interface means equipped with a function to display and output various information such as track ball, joystick, touch panel type LCD, control panel for ophthalmology examinations, and with a function to input various information.

The communication interface 1208 sends control signals from the CPU 1201 to each part of the fundus camera unit 1000A or of the OCT unit 1150, or receives detection signals output from the CCD 1184.

Moreover, when the computer 1200 is connected to a network such as LAN (Local Area Network), Internet, etc., the communication interface 1208 may be configured to be equipped with a network adapter such as a LAN card, etc. or communication equipment such as a modem, etc. so as to be able to perform data communication through the network. In this case, a server accommodating the control program 1204a may be installed, and at the same time, the computer 1200 may be configured as a client terminal of the server.

Control System Configuration

The configuration of the control system of the fundus observation device 1000 having the configuration described above is explained referring to FIG. 17. FIG. 17 shows a part related to the operations or processes of the present invention that has been particularly selected from among constituents composing the fundus observation device 1000.

The control system of the fundus observation device 1000 is configured such that the controlling part 1210 of the computer 1200 is in the center. The controlling part 1210 is an equivalent of one example of a "controlling means" of the present invention and is comprised including: a CPU 1201, a RAM 1202, a ROM 1203, a hard disk drive 1204 (control program 1204a), and a communication interface 1208.

The controlling part 1210 executes the above controlling processes by the CPU 1201 that is operated based on the control program 1204a. In particular, by controlling the mirror drive mechanisms 1241, 1242, 1243, 1244 of the fundus camera unit 1000A respectively, the Galvanometer mirrors 1141A, 1141B, the quick return mirror 1127, and the switching mirror 1129 respectively may be operated independently.

Furthermore, the controlling part 1210 controls the displaying of two kinds of images photographed by the fundus observation device 1000: that is, a 2-dimensional image (fundus image Ef) of the surface of a fundus oculi Ef by the fundus camera unit 1000A, and an image of a fundus oculi Ef formed based on the detection signal obtained by the OCT unit 1150, parallel to each other on the display 1207 of the user interface 1230.

The user interface (UI) 1230 is equipped with operational devices such as a keyboard 1205 or a mouse 1206, etc. and with a display device such as a display 1207, etc. This user interface 1230 constitutes one example of the "operating means" and "display means" of the present invention. The image processing part 1220 is configured including a CPU 1201, a RAM 1202, a ROM 1203, a hard disk drive 1204, etc.

The controlling feature of scanning the signal light LS by the controlling part 1210, the image forming process feature by the image processing part 1220, and the position correction process feature by the same image processing part 1220 are respectively described below.

Regarding Signal Light Scanning

Scanning of the signal light LS is performed by changing the facing direction of the reflecting surfaces of the Galvanometer mirrors 1141A and 1141B of the scanning unit 1141 in the fundus camera unit 1000A, as described above. By controlling the mirror drive mechanisms 1241 and 1242 respectively, the controlling part 1210 changes the facing direction of the reflecting surfaces of the Galvanometer mirror 1141A and 1141B, and scans the signal light LS on the fundus oculi Ef.

Once the facing direction of the reflecting surface of the Galvanometer mirror 1141A is changed, the signal light LS is scanned in a horizontal direction (x-direction in FIG. 13) on the fundus oculi Ef. Whereas, once the facing direction of the reflecting surface of the Galvanometer mirror 1141A is changed, the signal light LS is scanned in a vertical direction (y-direction in FIG. 13) on the fundus oculi Ef. Furthermore, by changing the facing direction of the reflecting surfaces of both Galvanometer mirrors 1141A and 1141B simultaneously, the signal light LS may be scanned in the combined x-direction and y-direction. That is, by controlling these two Galvanometer mirrors 1141A and 1141B, the signal light LS may be scanned in an arbitrary direction on the xy plane.

The scanning features of the signal light LS in the present embodiment are performed, for example, in the same way as the first embodiment. That is, as shown in FIG. 4 (A), the signal light LS is scanned within a rectangular shaped scanning region R that has been preset. Within this scanning region R, a plurality of (m number of) scanning lines R1 through Rm have been set in the x-direction. When the signal light LS is scanned along each scanning line Ri (i=1 through m), detection signals of interference light LC are generated.

Herein, the direction of each scanning line Ri is referred to as the main scanning direction and the orthogonally crossing direction is referred to as the sub-scanning direction. Therefore, scanning of the signal light LS in the main scanning direction is performed by changing the facing direction of the reflecting surface of the Galvanometer mirror 1141A, and scanning in the sub-scanning direction is performed by changing the facing direction of the reflecting surface of the Galvanometer mirror 1141B.

On each scanning line Ri, as shown in FIG. 4 (B), a plurality (n number of) of scanning points Ri1 through Rin have been preset.

In order to execute scanning as shown in FIG. 4, the controlling part 1210 controls the Galvanometer mirrors 1141A and 1141B to set the incident target of the signal light LS with respect to a fundus oculi Ef at a scan start position RS (scanning point R11) on the first scanning line R1. Subsequently, the controlling part 1210 controls the low coherence light source 1160 to flash the low coherence light L0 for emitting the signal light LS to the scan start position RS. The CCD 1184 receives the interference light LC based on the fundus reflection light of this signal light LS at the scan start position RS and outputs detection signals to the controlling part 1210.

Next, by controlling the Galvanometer mirror 1141A, the controlling part 1210 scans the signal light LS in the main scanning direction and sets the incident target at a scanning point R12, triggering a flash emission of the low coherence light L0 for making the signal light LS incident onto the scanning point R12. The CCD 1184 receives the interference light LC based on the fundus reflection light of this signal light LS at the scanning point R12, and then outputs the detection signal to the controlling part 1210.

Likewise, the controlling part 1210 obtains detection signals output from the CCD 1184 responding to the interference light LC with respect to each scanning point, by flash emitting the low coherence light L0 at each scanning point while shifting the incident target of the signal light LS from scanning points R13, R14, - - - , R1 (n−1), R1n in order.

Once measurement at the last scanning point R1n of the first scanning line R1 is finished, the controlling part 1210 controls the Galvanometer mirrors 1141A and 1141B simultaneously and shifts the incident target of the signal light LS to the first scanning point R21 of the second scanning line R2 following a line switching scan r. Then, by conducting the previously described measurement with regard to each scanning point R2j (j=1 through n) of this second scanning line R2, a detection signal corresponding to each scanning point R2j is obtained.

Likewise, a measurement with respect to each of the third scanning line R3, - - - , the m−1th scanning line R (m−1), the mth scanning line Rm is conducted to obtain the detection signals corresponding to each scanning point. Furthermore, the symbol RE on a scanning line Rm is a scan end position in accordance with a scanning point Rmn.

As a result, the controlling part 1210 obtains m×n number of detection signals corresponding to m×n number of scanning points Rij (i=1 through m, j=1 through n) within the scanning region R. Hereinafter, a detection signal corresponding to the scanning point Rij may be represented as Dij.

Such interlocking control of such shifting of scanning points and the output of the low coherence light L0 may be realized by synchronizing, for instance, the transmitting timing of control signals with respect to the mirror drive mechanisms 1241, 1242 and the transmitting timing of control signals (output request signal) with respect to the low coherence light source 1160.

Figure 18:
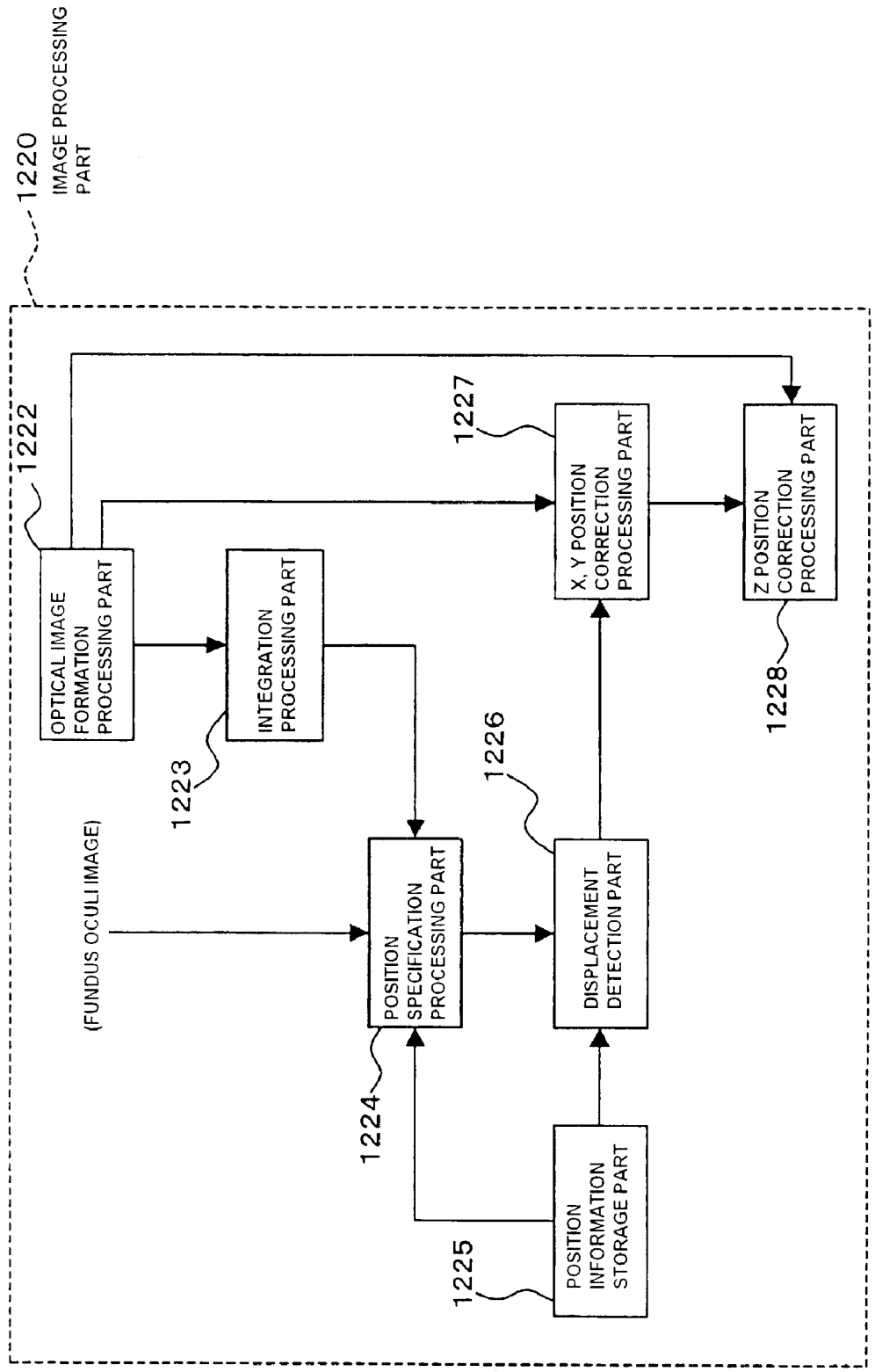
FIG. 18 is a schematic block diagram representing one example of the constitution of an image processing part in a control system of a preferred embodiment of the fundus observation device related to the present invention.

As described, when each Galvanometer mirror 1141A and 1141B is being operated, the controlling part 1210 stores the position of each scanning line Ri or the position of each scanning point Rij (coordinate on the xy coordinate system) on the position information storage part 1225 in the image processing part 1220 shown in FIG. 18. This stored content (scan positional information) is used in an image forming process as was conducted conventionally.

Regarding Image Formation Processing

With regard to image formation by an image processing part 1220, one example is explained. This image processing part 1220 is comprised including a CPU 1201, a RAM 1202, and a hard disk drive 1204 that are operated based on a control program 1204a. In addition, the processing to be explained below is performed by the optical image formation processing part 1222 in the image processing part 1220 shown in the block diagram of FIG. 18.

The image processing part 1220 forms tomographic images of a fundus oculi Ef along each scanning line Ri (main scanning direction), and forms a 3-dimensional image of the fundus oculi Ef based on these tomographic images.

The formation of a tomographic image along the main scanning direction is configured as was conventionally done including a 2-step arithmetic process. In the first step of the arithmetic process, based on a detection signal Dij corresponding to each scanning point Rij, an image Gij in the depth direction (z-direction in FIG. 13) of a fundus oculi Ef at the scanning point Rij is formed.

The tomographic image formed by the image processing part 1220 has, for example, the same features as in FIG. 6 of the first embodiment. In the second step of the arithmetic process, with regard to each scanning line Ri, based on the images Gi1 through Gin in the depth direction at the n number of scanning points Ri1 through Rin thereon, a tomographic image Gi of a fundus oculi Ef along this scanning line Ri is formed. Then, the image processing part 1220 determines the arrangement and the distance of each scanning point Ri1 through Rin while referring to the positional information (described above) of each scanning point Ri1 through Rin, forms this scanning line Ri via the above process, and m number of tomographic images G1 through Gm at different positions of the sub-scanning direction (y-direction) are obtained.

Next, the formation of a 3-dimensional image of a fundus oculi Ef is explained. A 3-dimensional image of a fundus oculi Ef is formed based on the m number of tomographic images obtained by the above arithmetic process. The image forming part 1220 forms a 3-dimensional image of the fundus oculi Ef by performing a well-known interpolating process to interpolate an image between the adjacent tomographic images Gi and G (i+1).

Then, the image processing part 1220 determines the arrangement and the distance of each scanning line Ri while referring to the positional information of each scanning line Ri to form this 3-dimensional image. For this 3-dimensional image, a 3-dimensional coordinate system (x, y, z) is set up, based on the positional information of each scanning point Rij and the z coordinate in the images Cij of the depth direction.

Furthermore, based on this 3-dimensional image, the image processing part 1220 is capable of forming a tomographic image of the fundus oculi Ef at a cross-section in an arbitrary direction other than the main scanning direction (x-direction). Once the cross-section is designated, the image processing part 1220 determines the position of each scanning point (and/or an image in the depth direction that has been interpolated) on this designated cross-section, and extracts an image (and/or image in the depth direction that has been interpolated) in the depth direction at each determined position to form a tomographic image of the fundus oculi Ef at the designated cross-section by arranging a plurality of extracted images in the depth direction.

Regarding Image Position Correction Processing

First, the constitution of the image processing part 1220 is explained. FIG. 18 is a block diagram showing one example of the constitution of the image processing part 1220.

The image processing part 1220 is provided with an integration processing part 1223, a position specification processing part 1224, a displacement detection part 1226, an xy position correction processing part 1227 and a z position correction processing part 1228, as well as the above-mentioned optical image formation processing part 1222 and position information storage part 1225.

The optical image formation processing part 1222 generates the optical image described above. In addition, on the position information storage part 1225, as described above, position information that indicates the positions of each scanning line Ri and xy coordinates of each scanning point Rij (that is, the measurement position of each tomographic image Gi or the measurement position of the image Gij of the depth direction) are stored. The position information storage part 1225 is the equivalent of one example of the "position storage means" of the present invention.

The integration processing part 1223 generates a 1-dimensional image (integrated image) by integrating each tomographic image Gi formed by the optical image formation processing part 1222 in the depth direction. In other words, it generates a point-like image by integrating each image Gij of the depth direction composing the tomographic image Gi in the depth direction (z-direction). Each point-like image indicates the integrated brightness in the depth direction at the position of the image Gij of the depth direction that was base thereof (the positions in the xy direction indicated in the above-mentioned position information are stored on the position information storage part 1225). Herein, "integrating in the depth direction" means the arithmetic process in which brightness values at each depth position of the image Gij of the depth direction are added together (projected).

By performing such a process with respect to all tomographic images Gi, a fundus image Ef' in the measurement region of the optical image and likewise an image showing the morphology of the fundus image Ef in that measurement region can be obtained. In other words, both a fundus image obtained by the fundus camera unit 1000A and an optical image obtained by the OCT unit 1150 are images formed from reflection light on the fundus surface and reflection light in the shallow region of the fundus tissue. Therefore, by integrating each tomographic image Gi obtained by scanning the 2-dimensional measurement region on the fundus oculi in depth direction and creating a 2-dimensional image, an image the same as the fundus image EF' in that measurement region can be obtained.

The position specification processing part 1224 determines the position of the above-mentioned integrated image in the fundus image Ef' that has been photographed by the fundus camera unit 1000A. More specifically, the position specification processing part 1224, with reference to the position information of each tomographic image stored on the position information storage part 1225, determines the position corresponding to this position information on the fundus image Ef'. Then, it searches the region having a similar brightness distribution as that of the integrated image (to be referred to as "corresponding region") from this specified position and the vicinity thereof. When the corresponding region cannot be found, it determines the targeted corresponding region by expanding the search range. This determined corresponding region is the position of the integrated image.

Furthermore, although the entire fundus image may be searched without referring to the tomographic image Gi, it is possible to shorten the searching time by using the position information as a guide for the search range.

The displacement detection part 1226 compares, for each tomographic image Gi, the position of the tomographic image Gi determined by the position specification processing part 1224 and the measurement position shown in the position information of the tomographic image Gi stored on the position information storage part 1225, and detects displacement in the direction perpendicular to their depth direction (that is, the xy-direction). For example, assuming that the determined coordinate with respect to an image Gij of a given depth direction consisting of the tomographic image Gi is P1 (x1, y1) and the stored coordinate is P2 (x2, y2), the displacement detection part 1226 detects the displacement of P1 and P2 by calculating $\{(x1-x2)^2+(y1-y2)^2\}^{(1/2)}$.

The xy position correction processing part 1227 corrects the displacement of each tomographic image Gi in the xy-direction based on the displacement of the position of each tomographic image Gi detected by the position detecting part 1226. That is, the position of the tomographic image Gi formed is moved by the optical image formation processing part 1222 by the amount of the detected displacement to process to fit in the position of the fundus image Ef'. The xy position correction processing part 1227 is the equivalent of one example of the "first image processing means."

The z position correction processing part 1228 performs the same process as the position correction processing part 43 in the first embodiment, which corrects the displacement of each tomographic image Gi in the depth direction (z-direction) by using an image for correction GR along the return scanning line RR (See FIGS. 5 and 6). In addition, the optical image formation processing part 1222 and the z position correction processing part 1228 compose one example of the "second image processing means" of the present invention.

Regarding the Display Feature of Images

Figure 20:
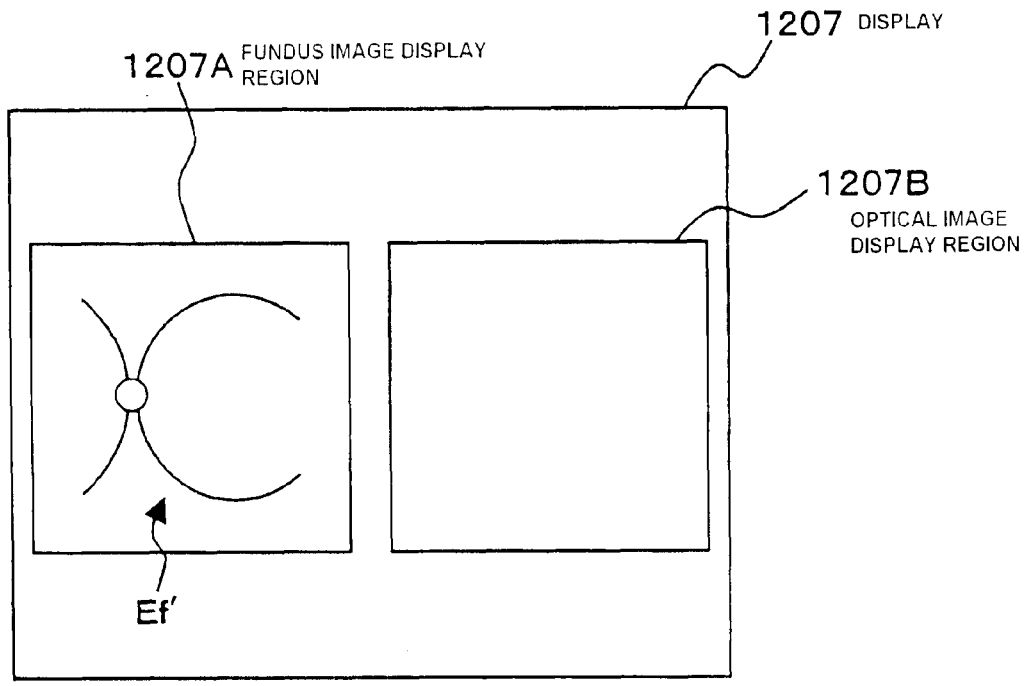
FIG. 20 is a schematic diagram representing one example of the display features of a fundus image in a preferred embodiment of the fundus observation device related to the present invention.

According to the fundus observation device 1000 of the present invention, two kinds of images, the fundus image Ef' by the fundus camera unit 1000A and the optical image (a tomographic image, a 3-dimensional image, etc.) by the OCT unit 1500, can be obtained. The fundus observation device 1000 can display these two kinds of images on the display 1207 respectively and display the two kinds of images in parallel. In the latter case of displaying in parallel, as shown in FIG. 20 to be described, the fundus image display region 1207A in which the fundus image Ef' is displayed and the optical image display region 1207B in which the optical image is displayed are formed on the display screen of the display 1207.

Operation

Figure 19:
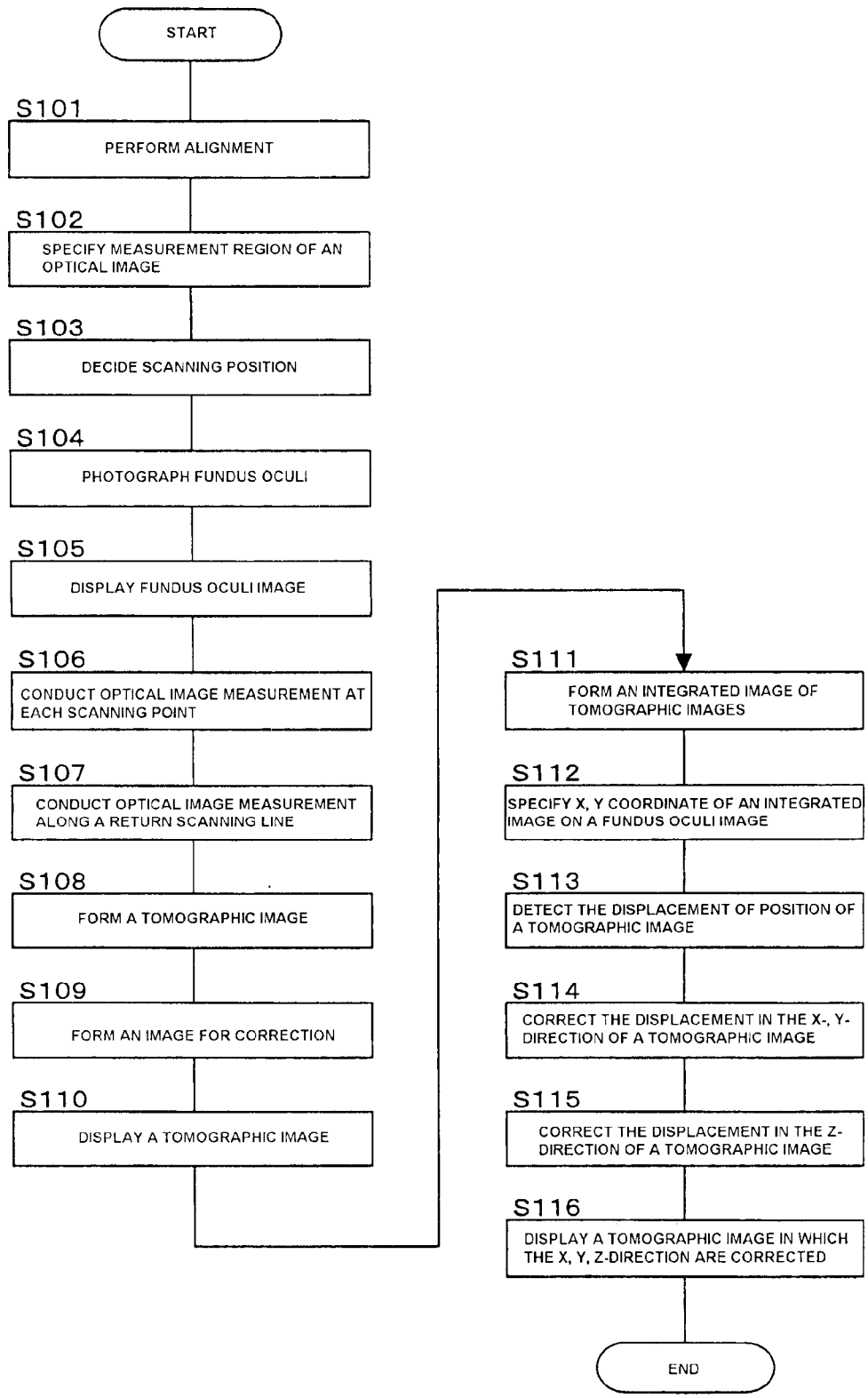
FIG. 19 is a flowchart representing one example of the operational features of a preferred embodiment of the fundus observation device related to the present invention.

The operation of the fundus observation device 1000 of the present embodiment having the constitution as above is explained. The flow chart shown in FIG. 19 shows one example of the operation of the fundus observation device 1000.

First, as a preparatory stage, the optical system is aligned for the fundus Ef to be measured (S101).

When the alignment is completed, the observation image of the fundus Ef is displayed on the display 1207 by lighting the halogen lamp 1101 of the fundus camera unit 1000A, and the measurement region in which the optical image is measured (scanning region R) is designated (S102). The controlling part 1210 determines the position of the scanning lines R1 through Rm and the scanning points R11 through Rmn in the designated measurement region (S103). These determined positions are stored on the position information storage part 1225 as position information. Herein, the position of the scanning line Ri is equivalent to the measurement position of the tomographic image Gi and the measurement position of the scanning line Rij is equivalent to the image Gij of the depth direction.

Next, a fundus image Ef' is photographed by flashing the xenon lamp 1103 of the fundus camera unit 1000A (S104). The photographed fundus image Ef' is displayed in the fundus image display region 1207A of the display 1207 by the controlling part 1210 as shown in FIG. 20 (S105).

Then, the OCT unit 1150 causes the signal light LS to scan in response to the control by the controlling part 1210 to perform the optical image measurement of each scanning point Rij (S106), and performs the optical image measurement along a return scanning line RR as in the first embodiment (S107).

Figure 21:
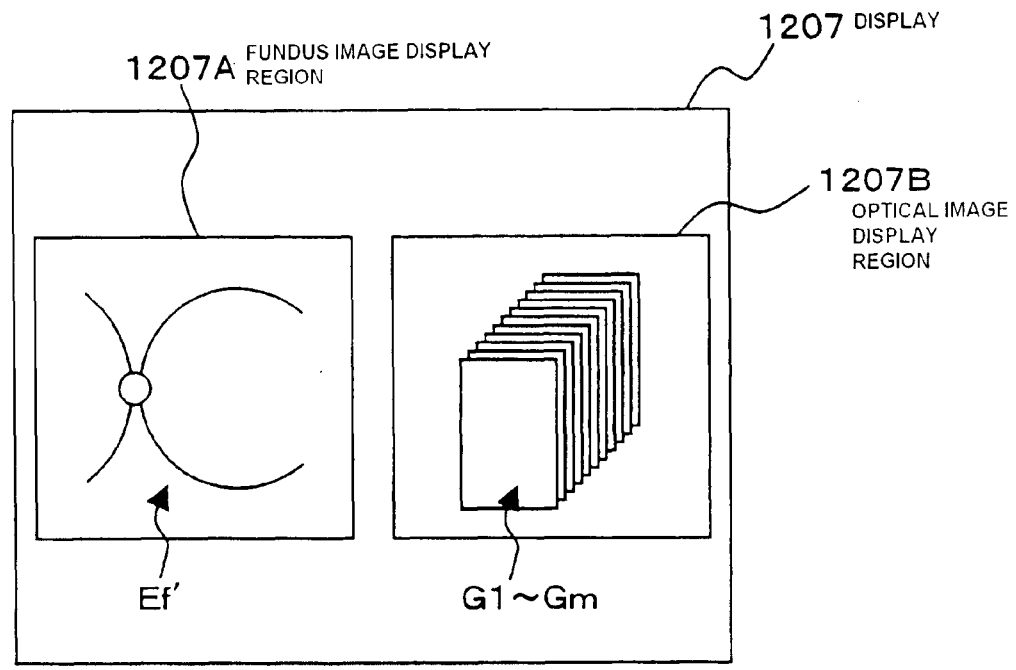
FIG. 21 is a schematic diagram representing one example of the display features of a fundus image in a preferred embodiment of the fundus observation device related to the present invention.

The optical image formation processing part 1222 forms the tomographic images G1 through Gm of the fundus Ef based on the measurement results at each scanning point Rij, and at the same time, forms the tomographic image for correction GR based on the measurement results along the return scanning line RR (S109). The tomographic images G1 through Gm formed at step S108 are, as shown in FIG. 21, displayed in the optical image display region 1207B of the display 1207 (S110).

Figure 22:
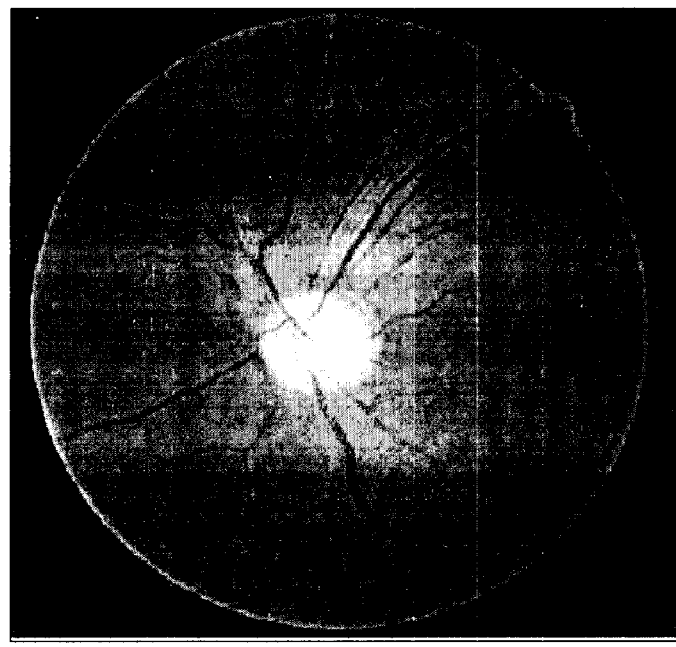
FIG. 22 is a diagram representing one fundus oculi image displayed by a preferred embodiment of the fundus observation device related to the present invention.
Figure 23:
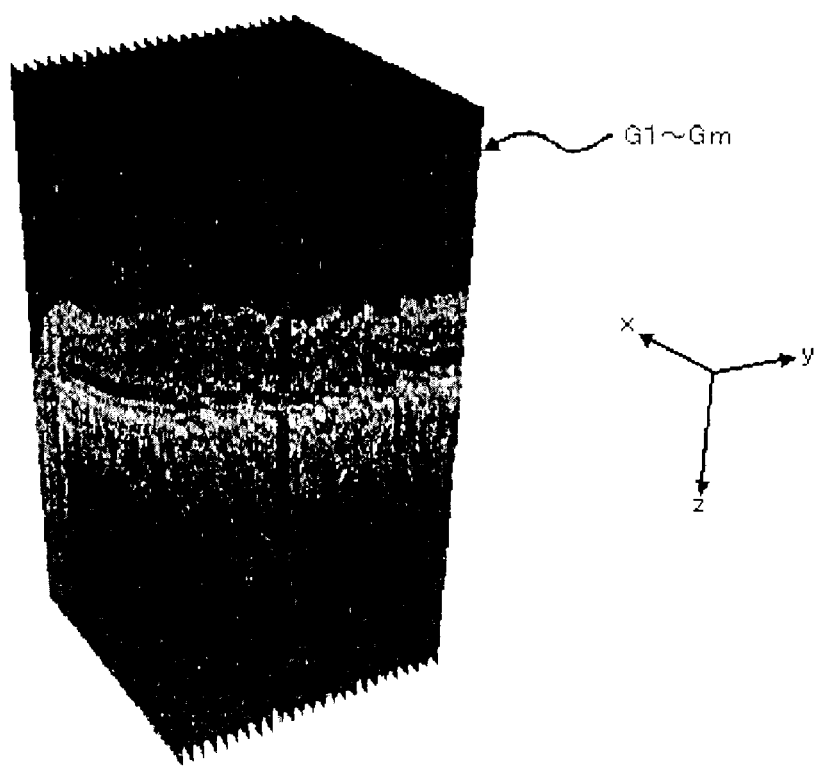
FIG. 23 is a diagram representing one tomographic image of a fundus oculi displayed by a preferred embodiment of the fundus observation device related to the present invention.

FIG. 22 shows a display example of an actual fundus image Ef', and FIG. 23 shows display examples of actual tomographic images G1 through Gm. The tomographic images G1 through Gm in FIG. 23 are arranged at intervals corresponding to each measurement position and are displayed as if they were 3-dimensional images of the fundus Ef.

Next, the integration processing part 1223 generates integrated images by integrating each tomographic image G1 through Gm in the depth direction (S111).

Figure 24:
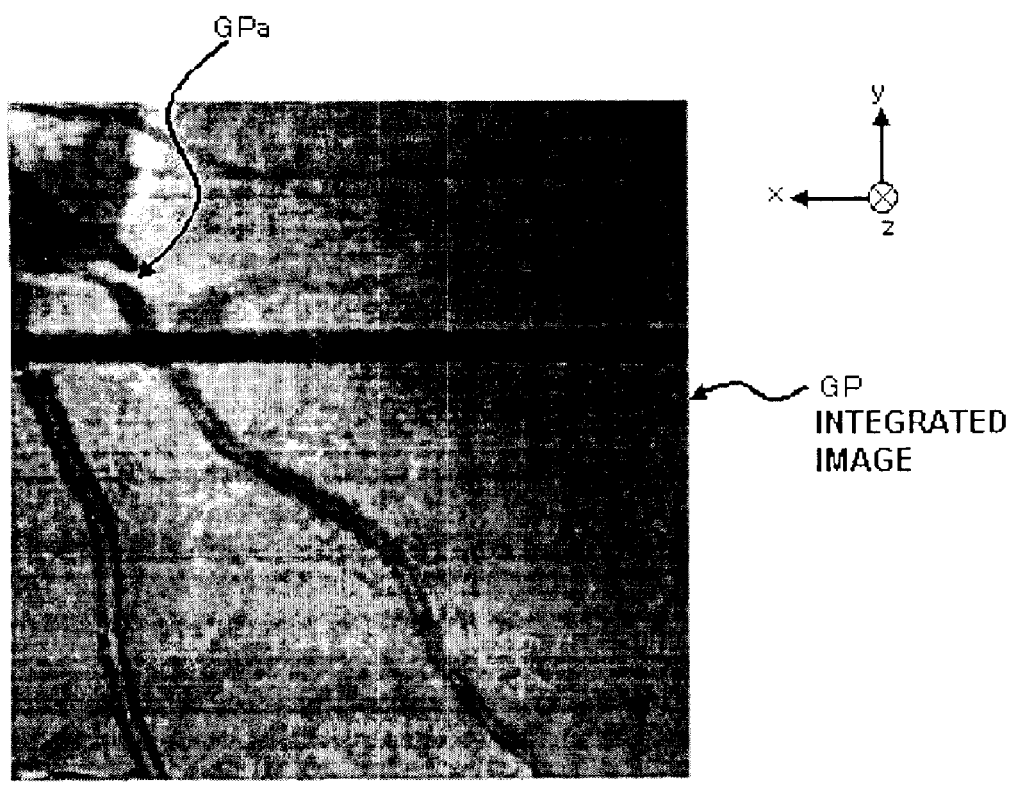
FIG. 24 is a diagram representing one integrated image generated by a preferred embodiment of the fundus observation device related to the present invention.

FIG. 24 shows integrated image GP obtained by integrating the tomographic images G1 through Gm in the FIG. 23. The integrated image GP is the image obtained by arranging in the y-direction a 1-dimensional image along the x-direction that was obtained integrating the tomographic image Gi.

In this integrated image GP, there is a part in which a blood vessel is broken in the image (blood vessel cut site GPa). This does not mean that the blood vessel is actually broken, and resulted from the fact that the eye to be examined E was misaligned in the x-direction due to ocular movement or heartbeat at the measurement time.

Then, the position specification processing part 1224 specifies the position (xy coordinates) of the integrated image on the fundus image Ef' (S112).

Next, the displacement detection part 1226, for each tomographic image Gi, compares the position of the tomographic image Gi determined at step S112 and the measurement position shown in the position information of the tomographic image Gi stored on the position information storage part 1225, and detects displacement in the xy-direction (S113).

Then, the x,y position correction processing part 1227 corrects the displacement in the xy-direction of each tomographic image Gi based on the displacement of each tomographic image Gi detected at step S113 (S114).

FIG. 25 shows a correction integrated image GP' obtained by correcting the displacement in the xy-direction of the integrated image in FIG. 24. The blood vessel cut site GPa in FIG. 24 is in a connected state in the correction integrated image GP'. This results from moving the position of each tomographic image Gi in the xy-direction and arranging them at the corresponding position in the fundus image Ef'.

In addition, black regions GPb' and GPc' near the upper right edge and the left edge of this correction integrated image are non-image parts due to having moved the tomographic image Gi in the x-direction. Therefore, it is found that the correction integrated image GP' has been created by moving the tomographic image on the upper side (+y-direction) of the integrated image GP in the left direction of the drawing (+x-direction) and moving the tomographic image on the bottom part in the right direction (−x-direction).

Finally, the z position correction processing part 1228 corrects the displacement in the z-direction of each tomographic image by using the tomographic image for correction GR formed at step S109 (S115), and displays the tomographic images G1 through Gm in which displacement in the xyz-direction has been corrected respectively in the optic image display region 1207B on the display 1207 (S116). The examiner undertakes a diagnostic evaluation with reference to the fundus image Ef' and the tomographic images G1 through Gm for which displacement have been corrected.

Action and Effect

Actions and effects given by the fundus observation device 1000 of the present embodiment operating as above are explained.

First, according to this fundus observation device 1000, a highly reliable image can be formed by effectively correcting the displacement of the optical image due to ocular movement and the like during optical image measurement. In particular, by using not only the same correction in the z-direction as in the first embodiment, but also the fundus image Ef', correction in the xy-direction can also be effectively performed.

Figure 27:
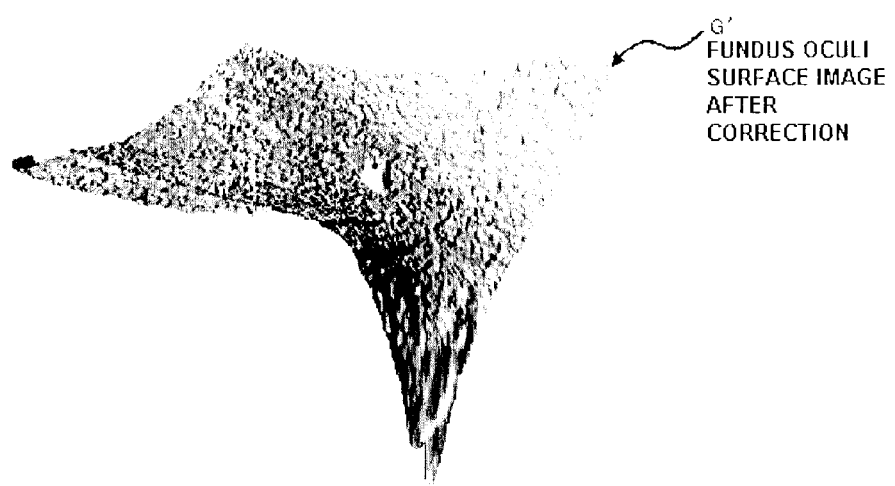
FIG. 27 is a diagram representing one fundus oculi surface image after correcting the displacement by a preferred embodiment of the fundus observation device related to the present invention.

Herein, referring to FIG. 26 and FIG. 27, the effects of correction of the displacement by the fundus observation device 1000 are explained. FIG. 26 shows the form of the surface image of the fundus retina (fundus oculi surface image before correction) G created from the tomographic image based on the data measured by the OCT unit 1150.

Furthermore, FIG. 27 shows the form of the fundus oculi surface image after correction G' obtained by giving corrections in the x, y and z-direction for this fundus oculi surface image before correction G.

The fundus oculi surface image before correction G in FIG. 26 is a very rough image that is rippling up and down (in z-direction). On the other hand, the fundus oculi surface image after correction G' in FIG. 27 is a smooth image that is close to the actual fundus surface. Thus, according to the fundus observation device 1000 of the present embodiment, very effective image correction can be provided.

In addition, the corrugated part on the fundus oculi surface image after correction G' is due to the effect of noise that is mixed in at the time of measurement. A known noise removal process can remove the effect of such noise.

Modified Example

The constitution described above is merely one example to preferably implement the image observation device of the present invention. Therefore, optional modifications may be implemented appropriately within the scope of the present invention. Hereinafter, one example of such modifications is explained.

First, although displacement correction in both the xy-direction and z-direction are performed in the above embodiment, it is possible to be configured to perform displacement correction in only the xy-direction. In that case, the z position correction processing part 1228 does not have to be provided in the block diagram of FIG. 18.

In addition, it is also possible to be configured to perform displacement correction in only the x-direction, or perform displacement in only the y-direction.

In the present embodiment described above, the fundus image is adapted to be photographed before performing the optical image measurement, but the timing to photograph the fundus image can be optionally determined. For example, it is also possible to photograph the fundus image after the optical image measurement or photograph the fundus image before and after the optical image measurement.

In the present embodiment described above, it is configured to generate integrated images for each tomographic image by integrating each tomographic image in the depth direction and to generate a 2-dimensional integrated image by arranging these 1-dimensional integrated images, but the generating method is not limited to this. For example, it is possible to form a 3-dimensional image from a tomographic image and generate a 2-dimensional integrated image by integrating this 3-dimensional image in the depth direction. In that case, displacement correction of the 3-dimensional image can be performed by specifying the position of the 2-dimensional integrated image in the fundus image and specifying distortion in the xy-direction (displacement) of the 2-dimensional image.

What is claimed is:

1. An optical image measuring device comprising:
    a light source;
    an interference light generating means for splitting the light output from said light source into a signal light directed toward an object to be measured and an reference light directed toward a reference object, and also for generating an interference light by overlaying the signal light that has passed through said object to be measured and the reference light that has passed through said reference object;
    a detecting means for outputting a detection signal upon receipt of said generated interference light;
    a scanning means for scanning the incident position of said signal light with respect to said object to be measured in a given main scanning direction and in a sub-scanning direction perpendicular to the main scanning direction respectively; and
    an image processing means for forming an image in the depth direction of said object to be measured at said incident position on the basis of said detection signal based on the interference light formed by said signal light that has passed through the incident position and said reference light and for forming a tomographic image along said two or more main scanning directions at different positions in said sub-scanning direction by forming the tomographic image along said main scanning direction based on said image at each of said formed incident positions, for each of a plurality of said incident positions along said main scanning direction; wherein
    said scanning means scans said signal light in the given direction crossing with said main scanning direction, and
    said image processing means forms a tomographic image for correction along said given direction and corrects the displacement of each of said two or more formed tomographic images based on said tomographic image for correction.

2. An optical image measuring device according to claim 1, wherein said image processing means corrects the displacement of said depth direction of each of said two or more tomographic images.

3. An optical image measuring device according to claim 2, wherein said image processing means corrects the displacement in the depth direction by adjusting the position of said image in the depth direction at the crossing position with said tomographic image for correction to the position of said image in the depth direction of said tomographic image for correction at said crossing position for each of said two or more tomographic images.

4. An optical image measuring device according to claim 3, wherein said correction of the displacement in said depth direction of each of said two or more tomographic images is performed by shifting said tomographic image to said depth direction so as to maximize the correlation value of normalization correlation between said image in the depth direction of said tomographic image and said image in the depth direction of said tomographic image for correction at said crossing position.

5. An optical image measuring device according to claim 3, wherein said correction of the displacement in said depth direction of each of said two or more tomographic images is performed by shifting said tomographic image to said depth direction so as to match the characterizing portion of said image in the depth direction of said tomographic image with the characterizing portion of said image in the depth direction of said tomographic image for correction at said crossing position.

6. An optical image measuring device according to claim 5, wherein said characterizing portion of said image in the depth direction is assumed to be the portion corresponding to the surface of said object to be measured.

7. An optical image measuring device according to claims 1, wherein said image processing means forms a 3-dimensional image of said object to be measured based on said two or more tomographic images,
    forms a new tomographic image along said given direction based on said formed 3-dimensional image, and corrects the displacement of each of said two or more tomographic images based on the displacement of said new tomographic image to said tomographic image for correction.

8. An optical image measuring device according to claims 2, wherein said image processing means forms a 3-dimensional image of said object to be measured based on said two or more tomographic images, forms a new tomographic image along said given direction based on said formed 3-dimensional image, and corrects the displacement of each of said two or more tomographic images based on the displacement of said new tomographic image to said tomographic image for correction.

9. An optical image measuring device according to claims 3, wherein said image processing means forms a 3-dimensional image of said object to be measured based on said two or more tomographic images, forms a new tomographic image along said given direction based on said formed 3-dimensional image, and corrects the displacement of each of said two or more tomographic images based on the displacement of said new tomographic image to said tomographic image for correction.

10. An optical image measuring device according to claims 4, wherein said image processing means forms a 3-dimensional image of said object to be measured based on said two or more tomographic images, forms a new tomographic image along said given direction based on said formed 3-dimensional image, and corrects the displacement of each of said two or more tomographic images based on the displacement of said new tomographic image to said tomographic image for correction.

11. An optical image measuring device according to claims 5, wherein said image processing means forms a 3-dimensional image of said object to be measured based on said two or more tomographic images, forms a new tomographic image along said given direction based on said formed 3-dimensional image, and corrects the displacement of each of said two or more tomographic images based on the displacement of said new tomographic image to said tomographic image for correction.

12. An optical image measuring device according to claims 6, wherein said image processing means forms a 3-dimensional image of said object to be measured based on said two or more tomographic images, forms a new tomographic image along said given direction based on said formed 3-dimensional image, and corrects the displacement of each of said two or more tomographic images based on the displacement of said new tomographic image to said tomographic image for correction.

13. An optical image measuring device according to claim 1, wherein said scanning means scans the incident position of said signal light in the specified direction of said main scanning direction when said two or more tomographic images are formed, and it is assumed that said specified direction is a direction connecting the ending position and the starting position of the scanning when said two or more tomographic images are formed.

14. An optical image measuring device according to claim 13, wherein said image processing means corrects the displacement of said depth direction of each of said two or more tomographic images.

15. An optical image measuring device according to claim 14, wherein said image processing means corrects the displacement in the depth direction by adjusting the position of said image in the depth direction at the crossing position with said tomographic image for correction to the position of said image in the depth direction of said tomographic image for correction at said crossing position for each of said two or more tomographic images.

16. An optical image measuring device according to claim 15, wherein said correction of the displacement in said depth direction of each of said two or more tomographic images is performed by shifting said tomographic image to said depth direction so as to maximize the correlation value of normalization correlation between said image in the depth direction of said tomographic image and said image in the depth direction of said tomographic image for correction at said crossing position.

17. An optical image measuring device according to claim 15, wherein said correction of the displacement in said depth direction of each of said two or more tomographic images is performed by shifting said tomographic image to said depth direction so as to match the characterizing portion of said image in the depth direction of said tomographic image with the characterizing portion of said image in the depth direction of said tomographic image for correction at said crossing position.

18. An optical image measuring device according to claim 17, wherein said characterizing portion of said image in the depth direction is assumed to be the portion corresponding to the surface of said object to be measured.

19. An optical image measuring device according to claims 13, wherein said image processing means forms a 3-dimensional image of said object to be measured based on said two or more tomographic images, forms a new tomographic image along said given direction based on said formed 3-dimensional image, and corrects the displacement of each of said two or more tomographic images based on the displacement of said new tomographic image to said tomographic image for correction.

20. An optical image measuring device according to claims 14, wherein said image processing means forms a 3-dimensional image of said object to be measured based on said two or more tomographic images, forms a new tomographic image along said given direction based on said formed 3-dimensional image, and corrects the displacement of each of said two or more tomographic images based on the displacement of said new tomographic image to said tomographic image for correction.

21. An optical image measuring device according to claims 15, wherein said image processing means forms a 3-dimensional image of said object to be measured based on said two or more tomographic images, forms a new tomographic image along said given direction based on said formed 3-dimensional image, and corrects the displacement of each of said two or more tomographic images based on the displacement of said new tomographic image to said tomographic image for correction.

22. An optical image measuring device according to claims 16, wherein said image processing means forms a 3-dimensional image of said object to be measured based on said two or more tomographic images, forms a new tomographic image along said given direction based on said formed 3-dimensional image, and corrects the displacement of each of said two or more tomographic images based on the displacement of said new tomographic image to said tomographic image for correction.

23. An optical image measuring device according to claims 17, wherein said image processing means forms a 3-dimensional image of said object to be measured based on said two or more tomographic images, forms a new tomographic image along said given direction based on said formed 3-dimensional image, and corrects the displacement of each of said two or more tomographic images based on the displacement of said new tomographic image to said tomographic image for correction.

24. An optical image measuring device according to claims 18, wherein said image processing means forms a 3-dimensional image of said object to be measured based on said two or more tomographic images, forms a new tomographic image along said given direction based on said formed 3-dimensional image, and corrects the displacement of each of said two or more tomographic images based on the displacement of said new tomographic image to said tomographic image for correction.

25. An optical image measuring program stored on a computer medium for controlling an optical image measuring device comprising:

a light source;

an interference light generating means for splitting the light output from said light source into a signal light directed toward an object to be measured and an reference light directed toward a reference object, and also for generating an interference light by overlaying the signal light that has passed through said object to be measured and the reference light that has passed through said reference object;

a detecting means for outputting a detection signal upon receipt of said generated interference light;

a scanning means for scanning the incident position of said signal light with respect to said object to be measured in a given main scanning direction and in a sub-scanning direction perpendicular to the main scanning direction respectively; and an image processing means for forming an image in the depth direction of said object to be measured at said incident position on the basis of said detection signal based on the interference light generated by said signal light that has passed through the incident position and said reference light and for forming a tomographic image along said two or more main scanning directions at different positions in said sub-scanning direction by forming the tomographic image along said main scanning direction based on said image at each of said formed incident positions, for each of a plurality of said incident positions along said main scanning direction; wherein said scanning means is controlled so as to scan said signal light in the given direction crossing with said main scanning direction, and said image processing means is made to form a tomographic image for correction along said given direction and to correct the displacement of each of said two or more formed tomographic images based on said tomographic image for correction.

26. A fundus observation device comprising:

a first image forming means for forming a 2-dimensional image of the surface of a fundus oculi of an eye to be examined; and a second image forming means for forming a tomographic image of said fundus oculi; wherein said fundus observation device comprises the first image processing means for generating an integrated image by integrating tomographic images formed by said second image forming means in the depth direction, for detecting displacement in the direction perpendicular to said depth direction of said generated integrated image based on said 2-dimensional image formed by said first image forming means, and for correcting the displacement of said tomographic images in said perpendicular direction based on said detected displacement.

27. A fundus observation device according to claim 26 further comprising: a position storage means for storing position information indicating the measurement position of a tomographic image formed by said second image forming means, wherein said detection of the displacement with said first image processing means is performed by specifying the position of said generated integrated image in a 2-dimensional image formed by said first image forming means and by detecting the displacement between said specified direction and said measurement position indicated in the stored position information in the direction perpendicular to said depth direction.

28. A fundus observation device according to claim 26 comprising:

a display means for displaying a 2-dimensional image formed by said first image forming means; and an operation means for specifying a measurement position of a tomographic image formed by said second image forming means on said displayed 2-dimensional image; wherein said detection of the displacement with said first image processing means is performed by specifying the position of said generated integrated image in a 2-dimensional image formed by said first image forming means, and by detecting the misplacement between said specified position and said specified measuring position in the direction perpendicular to said depth direction.

29. A fundus observation device comprising:

a first image forming means for forming a 2-dimensional image of the surface of a fundus oculi of an eye to be examined;

a light source; an interference light generating means for splitting the light output from said light source into a signal light directed toward said fundus oculi and an reference light directed toward a reference object, and also for generating an interference light by overlaying the signal light that has passed through said fundus oculi and the reference light that has passed through said reference object; a detecting means for outputting a detection signal upon receipt of said generated interference light; a scanning means for scanning the incident position of said signal light with respect to said fundus oculi in a given main scanning direction and in a sub-scanning direction perpendicular to the main scanning direction respectively; and a second image forming means for forming an image in the depth direction of said fundus oculi at said incident position on the basis of said detection signal based on the interference light generated by said signal light passing incident position and said reference light and for forming a tomographic image along said two or more main scanning directions at different positions in said sub-scanning direction by forming the tomographic image along said main scanning direction based on said image at each of said formed incident positions, for each of a plurality of said incident positions along said main scanning direction; wherein said fundus observation device comprises:

a first image processing means for generating each integrated image of said two or more tomographic images by integrating each of the two or more tomographic images formed by said second image forming means in said depth direction, for detecting displacement in the direction perpendicular to said depth direction of each of said formed two or more integrated images based on said 2-dimensional image formed by said first image forming means, and for correcting each displacement of said two or more tomographic images in said perpendicular direction based on said detected displacement;

a control means for controlling said scanning means of said second image forming means so as to scan said signal light in the given direction crossing with said main scanning direction; and a second image processing means for forming a tomographic image for correction along said given direction and for correcting the displacement in said depth direction of each of said formed two or more tomographic images based on said tomographic image for correction.

30. A fundus observation device according to claim 29 further comprising: a position storage means for storing position information indicating the measurement position of a tomographic image formed by said second image forming means, wherein said detection of the displacement with said first image processing means is performed by specifying the position of said generated integrated image in a 2-dimensional image formed by said first image forming means and by detecting the displacement between said specified direction and said measurement position indicated in the stored position information in the direction perpendicular to said depth direction.

31. A fundus observation device according to claim 29 comprising:

a display means for displaying a 2-dimensional image formed by said first image forming means; and an operation means for specifying a measurement position of a tomographic image formed by said second image forming means on said displayed 2-dimensional image; wherein said detection of the displacement with said first image processing means is performed by specifying the position of said generated integrated image in a 2-dimensional image formed by said first image forming means, and by detecting the misplacement between said specified position and said specified measuring position in the direction perpendicular to said depth direction.

32. A fundus oculi observing program stored on a computer readable medium that makes a fundus observation device function as:

a first image processing means for generating each integrated image of said two or more tomographic images by integrating each of said two or more tomographic images formed by said second image forming means in said depth direction, for detecting displacement in the direction perpendicular to said depth direction of said each of generated two or more integrated images based on the 2-dimensional image formed by said first image forming means, and for correcting each displacement of said two or more tomographic images at said perpendicular direction based on said detected displacement;

a control means for controlling said scanning means of said second image forming means so as to scan said signal light in the given direction crossing with said main scanning direction; and a second image processing means for forming a tomographic image for correction along said given direction and for correcting the displacement at said depth direction of each of said formed two or more tomographic images based on said tomographic image for correction, wherein said fundus observation device comprises:

a first image forming means for forming a 2-dimensional image of the surface of a fundus oculi of an eye to be examined;

a second image forming means comprising: a light source; an interference light generating means for splitting the light output from said light source into a signal light directed toward said fundus oculi and an reference light directed toward a reference object, and also for generating an interference light by overlaying the signal light that has passed through said fundus oculi and the reference light that has passed through said reference object; a detecting means for outputting a detection signal upon receipt of said generated interference light; a scanning means for scanning the incident position of said signal light with respect to said fundus oculi in a given main scanning direction and in a sub-scanning direction perpendicular to the main scanning direction respectively; and an image processing means for forming an image in the depth direction of said fundus oculi at said incident position on the basis of said detection signal based on the interference light generated by said signal light that has passed the incident position and said reference light and for forming a tomographic image along said two or more main scanning directions at different positions in said sub-scanning direction by forming the tomographic image along said main scanning direction based on said image at said each formed incident position, for each of a plurality of said incident positions along said main scanning direction.

* * * * *